US009782526B2

(12) United States Patent
Sherman et al.

(10) Patent No.: US 9,782,526 B2
(45) Date of Patent: Oct. 10, 2017

(54) DEVICE AND METHOD FOR COLLECTING AND DISPENSING COLOSTRUM

(71) Applicant: MATERNAL LIFE, LLC, Palo Alto, CA (US)

(72) Inventors: Jules P. Sherman, Palo Alto, CA (US); Rush L. Bartlett, II, Mountain View, CA (US); Ryan J. F. Van Wert, Palo Alto, CA (US)

(73) Assignee: Maternal Life, LLC., Palo Alto, CA (US)

( * ) Notice: Subject to any disclaimer, the term of this patent is extended or adjusted under 35 U.S.C. 154(b) by 30 days.

(21) Appl. No.: 14/624,363

(22) Filed: Feb. 17, 2015

(65) Prior Publication Data
US 2015/0196696 A1    Jul. 16, 2015

Related U.S. Application Data

(63) Continuation-in-part of application No. 13/945,751, filed on Jul. 18, 2013, now Pat. No. 8,979,819, which
(Continued)

(51) Int. Cl.
*A61M 1/06* (2006.01)
*A61M 39/10* (2006.01)
(Continued)

(52) U.S. Cl.
CPC ............ *A61M 1/068* (2014.02); *A61M 39/10* (2013.01); *A61J 7/0053* (2013.01); *A61J 15/0003* (2013.01); *A61M 2209/084* (2013.01)

(58) Field of Classification Search
CPC ........ A61M 1/068; A61M 39/10; A61M 1/06; A61M 2209/084; A61J 7/0053; A61J 15/0003
See application file for complete search history.

(56) References Cited

U.S. PATENT DOCUMENTS 3,911,920 A    10/1975  Susinn
4,323,067 A *   4/1982  Adams ................... A61M 1/06
                                                    604/346
(Continued)

FOREIGN PATENT DOCUMENTS

JP         2003-299727        10/2003

OTHER PUBLICATIONS

International Search Report, dated Dec. 22, 2014 in PCT Application Serial No. PCT/US14/054377, dated Dec. 22, 2014, 1-2.
(Continued)

*Primary Examiner* — Kevin C Sirmons
*Assistant Examiner* — Amber Stiles
(74) *Attorney, Agent, or Firm* — Merchant & Gould P.C.

(57) ABSTRACT

A device for collecting colostrum from a breast of a human and dispensing the colostrum to a newborn may include a colostrum collection member and a plunger. The colostrum collection member may include a funnel-shaped proximal portion with a wide, open end for facilitating collection of expressed colostrum, a narrow distal portion with a small-diameter opening for dispensing the expressed colostrum to the newborn, and a cylindrical barrel portion between the funnel-shaped proximal portion and the narrow distal portion. The plunger is configured for advancement through the wide, open end and the barrel portion of the collection member to force the colostrum out of the small-diameter opening.

7 Claims, 29 Drawing Sheets

Related U.S. Application Data is a continuation-in-part of application No. 13/923,264, filed on Jun. 20, 2013, now Pat. No. 8,998,879, which is a continuation-in-part of application No. 13/447,186, filed on Apr. 14, 2012, now abandoned.

(60) Provisional application No. 61/780,804, filed on Mar. 13, 2013, provisional application No. 61/475,578, filed on Apr. 14, 2011.

(51) Int. Cl.
    *A61J 7/00*     (2006.01)
    *A61J 15/00*     (2006.01)

(56) References Cited

U.S. PATENT DOCUMENTS

| | | |
|---|---|---|
| 5,941,847 A | 8/1999 | Huber et al. |
| RE36,324 E | 10/1999 | Yoda et al. |
| 6,200,295 B1 * | 3/2001 | Burchett ............... A61J 7/0046 222/133 |
| 6,210,360 B1 * | 4/2001 | Kong ..................... A61M 1/06 604/315 |
| 6,884,229 B2 | 4/2005 | Renz |
| 7,048,120 B2 | 5/2006 | Pond |
| 7,648,467 B2 | 1/2010 | Wang |
| 8,360,102 B2 | 1/2013 | Khouri |
| 8,979,819 B2 | 3/2015 | Sherman et al. |
| 8,998,879 B2 | 4/2015 | Sherman et al. |
| 9,248,077 B1 * | 2/2016 | Kelly .................... A61M 1/062 |
| 2002/0156419 A1 | 10/2002 | Silver |
| 2007/0118078 A1 | 5/2007 | McNally et al. |
| 2009/0227943 A1 | 9/2009 | Schultz |
| 2009/0254028 A1 | 10/2009 | Brittner |
| 2010/0049122 A1 * | 2/2010 | Jaeger-Waldau ....... A61M 1/06 604/74 |
| 2011/0054436 A1 | 3/2011 | Griffis et al. |
| 2011/0168292 A1 | 7/2011 | Luzbetak et al. |
| 2011/0251552 A1 | 10/2011 | Brittner |
| 2012/0232524 A1 * | 9/2012 | Hyun ..................... A61M 5/385 604/514 |
| 2013/0005023 A1 | 1/2013 | Min |
| 2013/0030379 A1 | 1/2013 | Ingram et al. |
| 2014/0135683 A1 * | 5/2014 | Hradisky ................ A61M 1/06 604/74 |

OTHER PUBLICATIONS

Written Opinion of the International Searching Authority, dated Dec. 22, 2014 in PCT Application Serial No. PCT/US14/054377, dated Dec. 22, 2014, 1-5.

* cited by examiner

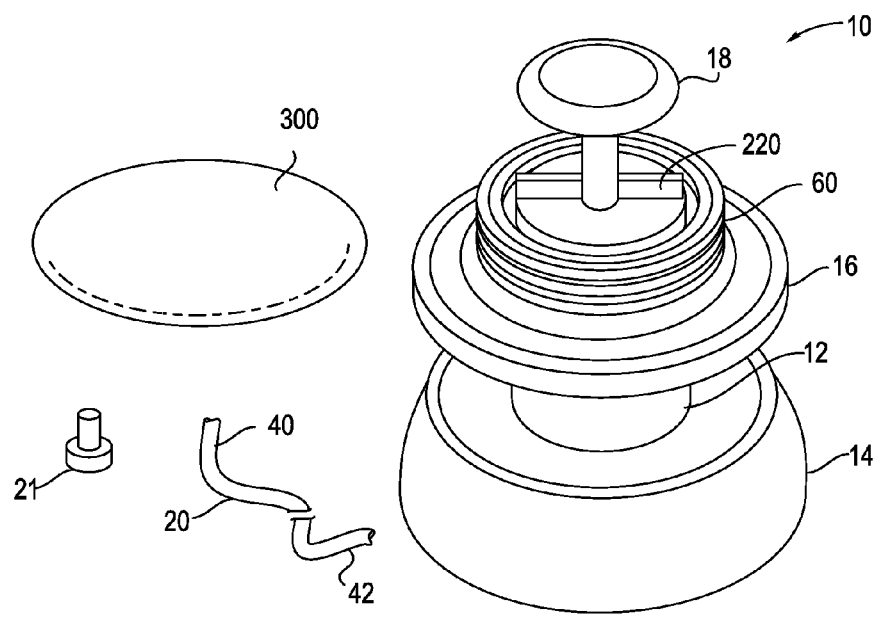
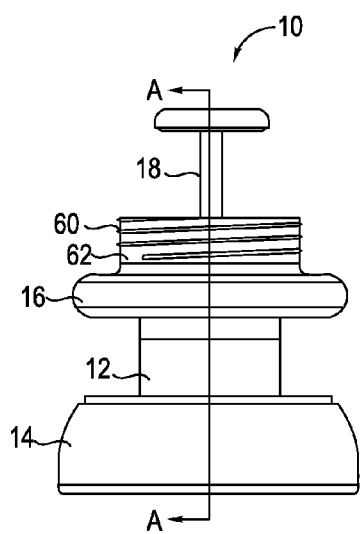
FIG. 2
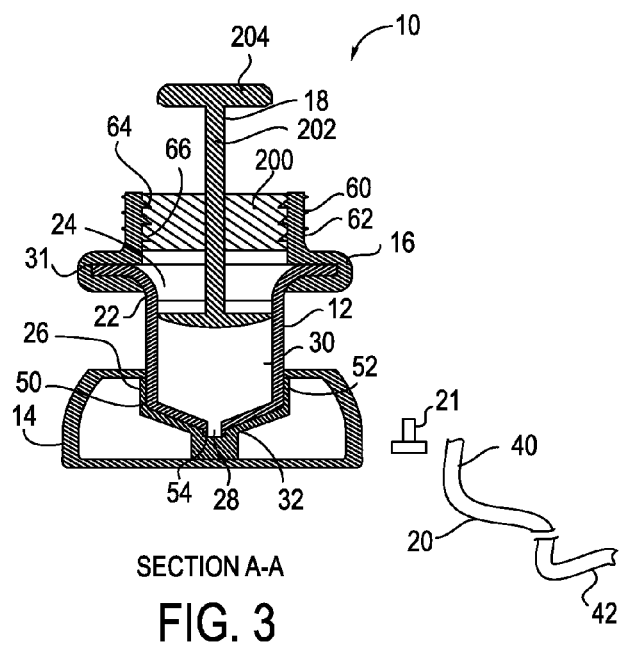
SECTION A-A
FIG. 3

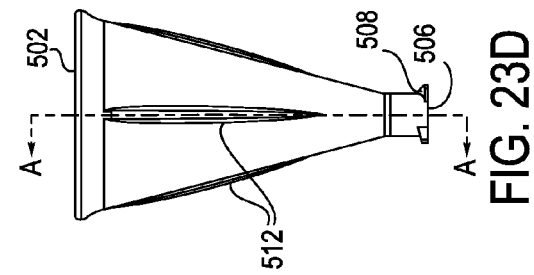
FIG. 23D
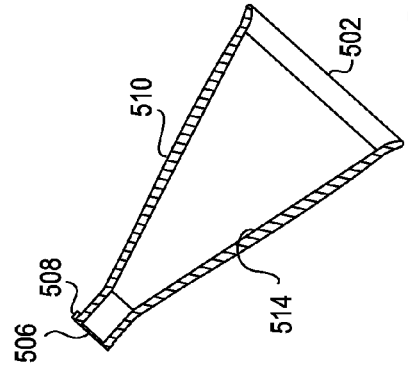
FIG. 23G
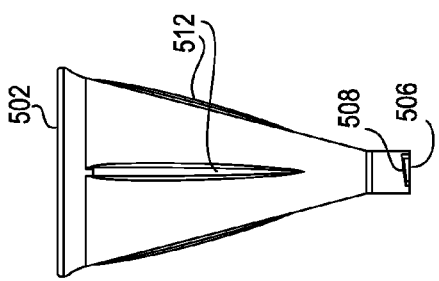
FIG. 23C
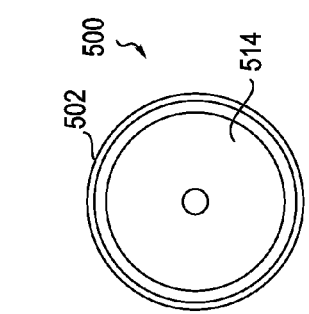
FIG. 23B
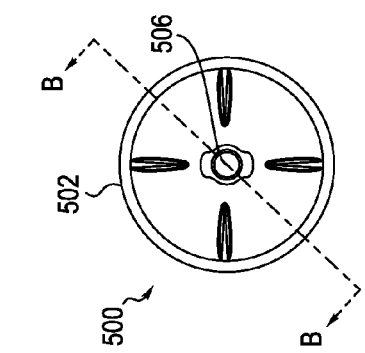
FIG. 23F
FIG. 23A
FIG. 23E

DEVICE AND METHOD FOR COLLECTING AND DISPENSING COLOSTRUM

CROSS-REFERENCE TO RELATED APPLICATION(S)

This application is a continuation-in-part of U.S. patent application Ser. No. 13/945,751, entitled "Device and Method for Collecting and Dispensing Colostrum," filed Jul. 18, 2013, now U.S. Pat. No. 8,979,819, which is a continuation-in-part of U.S. patent application Ser. No. 13/923,264, entitled, "Device and Method for Collecting and Dispensing Colostrum," filed Jun. 20, 2013, now U.S. Pat. No. 8,998,879, which is a continuation-in-part of U.S. patent application Ser. No. 13/447,186, filed Apr. 14, 2012, entitled "Systems and Methods for Collecting, Storing, and Administering Fluid from a Breast," which claims the benefit of U.S. Provisional Application No. 61/780,804, filed on Mar. 13, 2013, entitled "Device and Method for Collecting and Dispensing Colostrum," and U.S. Provisional Application No. 61/475,578, filed on Apr. 14, 2011, entitled "Systems and Methods for Collecting, Storing, and Administering Fluid from a Breast." The above-referenced applications are all hereby incorporated by reference in their entirety for all purposes.

TECHNICAL FIELD

The present application pertains generally the field of medical devices. More specifically, the present application pertains to devices, systems and methods for collecting colostrum from a breast and dispensing the colostrum to a newborn baby.

BACKGROUND

Colostrum is fluid produced by the mammary glands of mammals in late stage of pregnancy, such as just prior to giving birth, and sometimes even after pregnancy. Colostrum is the first nutritional liquid that comes out of the breast during lactation. Colostrum has higher protein content than ordinary milk, and contains antibodies to protect the newborn against disease. This highly nutritional liquid is packed with antibodies and other immune enhancing substances and is thus very important for healthy new born development. Colostrum is essentially newborn's first food, and helps the newborn transition to consumption of mature milk. Thus, it is important that colostrum be fed to newborns after birth.

Colostrum is produced at a very slow rate of several milliliters per hour and generally requires some form of pumping and or hand expression to cause it to exit the breast. In the first few days after birth, it is extremely important to breastfeed a newborn at least 8-12 times each 24 hours, and more often is even better. This allows the baby to get all the benefits of the colostrum and also stimulates production of a plentiful supply of mature milk.

Collection of colostrum is difficult, due to the small amount of volume produced, and existing breast milk pumps are not designed for the higher viscosity colostrum and/or the small volumes of colostrum produced and expressed from the breast. Besides pumps for breast milk, the generally accepted practice is to use whatever container is available to collect the colostrum. This could be a spoon, small cup, or small vial. Usually all of these containers require transfer to another container for administering (such as a syringe). This transfer of material leads to loss of colostrum when every precious drop counts.

Various techniques may be used to provide colostrum to newborn. For example, a medicine cup or a plastic spoon may be used to collect the colostrum from the mother's breast(s). In some cases, the collected colostrum is then transferred to a syringe, which is then used to administer the colostrum to the newborn. In other cases, the colostrum is administered to the baby directly from the cup or spoon.

In the case of humans, in certain situations, the newborn may be separated from the mother immediately after birth. For example, the newborn may need to be treated right after birth, such as due to premature birth, infection, or other medical conditions. In such cases, the mother would not be able to directly feed the newborn from her breasts. Other cases, such as maternal pain, newborn inability to effectively suck, etc., often prevent direct breast feeding in the early postpartum stage. Also, a mother may choose not to directly breastfeed the newborn, and may elect, instead, to use a device for administering the colostrum to the newborn.

Generally, the currently used techniques and devices for collecting and administering colostrum have a number of drawbacks. First, the current techniques involve expressing the colostrum into a first container, and then using a second, separate device, such as a syringe, to remove the colostrum from the first container and dispense it to the newborn. This process exposes the colostrum to air and thus possible germ contact, is inconvenient for mothers, and typically wastes at least some amount of colostrum in the transfer process. Second, the current techniques generally involve expressing colostrum into a relatively large container, such as a plastic cup or breast pump bottle. Colostrum is naturally produced in very small volumes, but mothers trying to express colostrum may often get discouraged when the colostrum appears to be incredibly small-volume relative to a large container. In summary, the current techniques do not work well for many nursing mothers and often cause a woman to give up on breast feeding during the first few days of a newborn's life.

Therefore, it would be desirable to provide methods, devices and systems for collecting colostrum from a breast and storing and/or dispensing the colostrum. Ideally, these methods, devices and systems would be easy to use and not intimidating to mothers. The methods, devices and systems would also ideally transfer colostrum from breast to newborn in an efficient way, so that very little colostrum is lost in the process.

BRIEF SUMMARY

The embodiments described herein relate to methods, systems and devices for collecting and dispensing colostrum. Although the embodiments will be described for use in collecting and dispensing colostrum, some or all embodiments may also be used for collecting and dispensing breast milk. Certain words will be used in this application to describe various embodiments, and these words should not be interpreted overly narrowly. For example, the term "system" or the phrase "connected system" may be used to describe a colostrum collection/administration system with multiple parts, at least some of which attach together during at least some portion of a collection/administration method. In various embodiments, these systems may include fewer or additional components, some of which attach and others of which may not attach. Similarly, the terms "dispensing" and "administering" may be used interchangeably, as may any other suitable synonym or similar word describing an action of feeding colostrum (and/or milk, in some embodiments) to a newborn.

One of the primary advantages of the methods, systems and devices described herein, which will be further explained below, is that they involve collecting colostrum in a device or connected system that is then conveniently used to administer the colostrum to the newborn. In other words, there is no need for transferring the colostrum from a first, collection vessel to a second, administration vessel. Although most if not all embodiments involve some kind of interface device for helping collect the colostrum, the interface device is connected, either directly or indirectly, to a colostrum administration device, such as a syringe or other suction-generating member. The syringe or other suction member can be actuated to draw the colostrum into a collection portion of the syringe or suction member, and then it can be removed from the interface and used to deliver the colostrum to the newborn.

In one embodiment, an interface device may be a colostrum collection device that is used to collect manually expressed colostrum and help direct it into a syringe or other containment/delivery device. In another embodiment, an interface device may be a breast pump shield adapter that is connected between a breast pump shield and a syringe or other containment/delivery device to direct colostrum from the breast shield into the containment/delivery device. In yet another embodiment, an interface device may be a combination colostrum collection device for use in manual expression and an adapter for use with a breast shield. Such a device may thus be used for both manual expression and breast pump expression of colostrum.

In one aspect, a method of using a system to collect colostrum from a breast of a human and using at least part of the system to dispense the colostrum to an newborn may involve: coupling an interface member with a suction member to form at least part of the system; positioning the interface member in contact with or near the breast; expressing colostrum from the breast, into the interface member; applying suction force to the interface member, using the suction member, to draw the colostrum into the suction member; detaching the interface member from the suction member; and dispensing the colostrum to the newborn from the suction member. In various alternative embodiments, the interface member may include, but is not limited to, a funnel, a suction cup, a bulb, a dome, a breast shield, a breast pump suction cup, a breast pump flange or an adapter.

In some embodiments, coupling the interface member with the suction member involves directly attaching the interface member to the suction member. In some of these embodiments, the suction member may be a syringe, one end of the interface member may include at least one thread on an outer surface, and attaching the interface member to the syringe may involve threading the at least one thread into at least one complementary thread on the syringe.

In some alternative embodiments, coupling the interface member with the suction member may involve coupling a first end of an adapter with the suction member, where the adapter is part of the system, and coupling a second end of the adapter with the interface member. In some of these embodiments, the suction member may be a syringe, the first end of the adapter may include at least one thread on an outer surface, and attaching the first end to the syringe may involve threading the thread into at least one complementary thread on the syringe. In some embodiments, the method may also include, before coupling the adapter with the suction member, selecting an adapter from a container holding at least three adapters, where each of the at least three adapters is configured to be used for one day of colostrum collection. In some embodiments, the interface member may be a breast pump shield, and the method may further include activating the breast pump to help pump colostrum from the breast.

In some embodiments, colostrum may be expressed, at least in part, via manual expression. In some embodiments, the step of positioning the interface member in contact with or near the breast may involve forming a seal between the interface member and a surface of the breast. In various alternative embodiments, the suction member may include, but is not limited to, a syringe, a bulb suction device, a cartridge or a vial. In embodiments where the suction member is a syringe, for example, dispensing the colostrum may involve positioning a distal end of the syringe in the newborn's mouth and pushing a plunger of the syringe to advance the colostrum out of the distal end of the syringe and into the newborn's mouth or nose. Alternatively, the method may further involve attaching a flexible tube to the syringe, after detaching the interface member, advancing a free end of the flexible tube into the newborn's mouth or nose and dispensing the colostrum to the newborn through the flexible tube.

In some embodiments, the interface member may be gripped using at least one ergonomic feature of the interface member. For example, such an ergonomic feature may include, but is not limited to, an overall shape, grooves, vertical protrusions, horizontal protrusions, diagonal protrusions and/or bumps. In various embodiments, the method may optionally include, before the coupling step, selecting the interface member from a package containing any suitable number of interface members.

Optionally, in some embodiments, the method may further involve using the system to collect breast milk from the breast and dispense the breast milk to the newborn. Also optionally, the method may involve storing the colostrum in the suction member before dispensing it to the newborn. In some embodiments, coupling the interface member with the suction member may involve engaging a locking member on the interface member with a complementary locking member on the suction member. In some embodiments, coupling the interface member with the suction member may form a seal between the interface member and the suction member. Optionally, some embodiments may include a step of coupling the interface member with a breast pump device before, during or after any step of the method.

In another aspect, a method of collecting colostrum from a breast of a human and dispensing the colostrum to a newborn may involve: coupling a first end of an adapter with a syringe; positioning a second end of the adapter in contact with or near the breast; manually expressing colostrum from the breast into the second end of the adapter; coupling the second end of the adapter with a breast pump shield; expressing colostrum from the breast, using the breast pump shield and a breast pump system attached to the breast pump shield; retracting a plunger of the syringe to cause the colostrum to move into the syringe from the adapter; detaching the adapter from the first end of the syringe; and dispensing the colostrum to the newborn from the syringe.

In some embodiments, coupling the first end of the adapter with the syringe may involve engaging threads on the adapter with complementary threads on the syringe. Alternatively, coupling the first end of the adapter with the syringe may involve press fitting a tapered distal end of the syringe into a tapered inner surface of the first end of the adapter. In some embodiments, coupling the second end of the adapter with the breast pump shield may involve engaging threads on the adapter with complementary threads on the breast pump shield.

In some embodiments, the step of manually expressing colostrum may precede the steps of coupling the steps of coupling the second end of the adapter with the breast pump shield and expressing colostrum from the breast, using the breast pump shield. Alternatively, the steps of coupling the second end of the adapter with the breast pump shield and expressing colostrum from the breast, using the breast pump shield, may precede the step of manually expressing colostrum, and wherein the method further includes detaching the breast pump shield from the adapter before the manual expression step.

In some embodiments, the method may further involve, after manually expressing the colostrum but before coupling the adapter with the breast pump shield, retracting the plunger of the syringe to cause the colostrum to move into the syringe from the adapter, wherein the retracting step is performed again after expressing colostrum from the breast, using the breast pump shield. In some embodiments, the method may further involve, before coupling the adapter with the syringe, selecting an adapter from a kit containing multiple adapters configured to attach to multiple different types of syringes. In some embodiments, dispensing the colostrum may involve positioning a distal end of the syringe in the newborn's mouth and pushing a plunger of the syringe to advance the colostrum out of the distal end of the syringe and into the newborn's mouth.

In another aspect, a combination collection/adapter device for facilitating the collection and administration of colostrum from a breast of a human to a newborn may include: a large-diameter end for collecting manually expressed colostrum and for attaching to a breast pump shield; at least one breast pump shield thread at or near the large-diameter end for coupling with one or more complementary threads on the breast pump shield; a small-diameter end for attaching to a syringe; at least one syringe thread on an external surface of the device at or near the small-diameter end for coupling with one or more complementary threads on a first type of syringe; a tapered inner surface of the small-diameter end, configured to mate with a distal end of a second type of syringe via press fit; and a tapered outer surface extending from the large-diameter end to the small-diameter end and configured to facilitate holding the device with one hand. Optionally, the device may further include at least one ergonomic feature disposed along the tapered surface for facilitating holding of the device. For example, the ergonomic feature may include, but is not limited to, an overall shape, grooves, vertical protrusions, horizontal protrusions, a textured surface, diagonal protrusions and/or bumps.

In another aspect, a device for collecting and administering fluid from a breast includes a container having a first end with a first opening for collecting fluid from the breast, and a second end with a second opening for administering the collected fluid, the second opening being smaller than the first opening, and a coupler for detachably coupling to the first end of the container, wherein the coupler comprises threads on an exterior surface for detachably coupling to a pump connector.

In another aspect, a device for collecting and administering fluid from a breast includes a container having a first end with a first opening for collecting fluid from the breast, and a second end with a second opening for administering the collected fluid, the second opening being smaller than the first opening, and a plunger configured to detachably couple to the first end of the container, wherein the container comprises a lip at the first end that circumferentially surrounds the first opening.

In another aspect, a method for collecting and administering fluid from a breast includes detachably coupling a pump connector to a container, the pump connector being a component of a pump system, wherein the container has a first end with a first opening, and a second end with a second opening, using the pump system to collect fluid from the breast, and using the container to receive the fluid through the first opening at the first end.

In another aspect, a kit for collecting and administering fluid from breast may include multiple units or parts of units of any of the devices described herein. For example, in one embodiment, a plastic bag may contain 20 parts and one instructions-for-use pamphlet. The 20 parts may include multiple funnels and adapters throughout a 2-day hospital stay. Each funnel and each adapter may be packaged individually to retain sterility. In another embodiment, a carton box may contain 20 "kit bags" and one instructions-for-use pamphlet. Each kit bag may contain a sterile funnel and sterile adapter. This kit bag may be adequate for a 4-6 hour period, for example. Any kit embodiment may also optionally include one or more feeding syringes. In some embodiments, for example the interfaces of the system/kit may be made by one manufacturer and packaged by that manufacturer with syringe(s) made by another manufacturer. Any of these kit embodiments may be advantageous for some hospitals, physicians, nurses and/or patients, for enhancing ease of use. Another optional feature of any of the kit embodiments may be an app or youtube link that shows a video of a mother using a device from the kit to further help the mother and nurse understand usage. A web link or app name could be printed on the instructions-for-use pamphlet, for example.

In another aspect, a method of collecting colostrum from a breast of a human and dispensing the colostrum to a newborn may involve: coupling a narrow end of a funnel-shaped colostrum collection device with a syringe; manually expressing colostrum from the breast into a wide end of the colostrum collection device that is opposite the narrow end; retracting a plunger of the syringe to create a suction force and thus cause the colostrum to move from the colostrum collection device into a barrel of the syringe; detaching the colostrum collection device from the syringe; and dispensing the colostrum to the newborn from the syringe without transferring the colostrum to any other colostrum container. In some embodiments, the coupling step involves threading at least one thread on the narrow end of the colostrum collection device into at least one complementary thread on the syringe. In some embodiment, the coupling step involves attaching a press fit surface on the narrow end of the colostrum collection device with a complementary press fit surface on the syringe. In some embodiments, dispensing the colostrum involves inserting a distal end of the syringe into the newborn's mouth and depressing the plunger of the syringe to force the colostrum out of the distal end and into the newborn's mouth.

In another aspect, a method of collecting colostrum from a breast of a human and dispensing the colostrum to a newborn may involve manually expressing colostrum from the breast into an open end of a funnel-shaped portion of a colostrum collection device, inserting a plunger of the colostrum collection device into the open, proximal end of the funnel-shaped portion, and depressing the plunger to force the colostrum out of a narrow, distal end of the colostrum collection device and into the newborn's mouth. Some embodiments may further involve measuring an amount of the expressed colostrum by viewing a fluid level indicator on a side of the colostrum collection device.

In another aspect, a device for collecting colostrum from a breast of a human and dispensing the colostrum to a newborn may include a colostrum collection member and a plunger. The colostrum collection member may include a funnel-shaped proximal portion with a wide, open end for facilitating collection of expressed colostrum, a narrow distal portion with a small-diameter opening for dispensing the expressed colostrum to the newborn, and a cylindrical barrel portion between the funnel-shaped proximal portion and the narrow distal portion. The plunger is configured for advancement through the wide, open end and the barrel portion of the collection member to force the colostrum out of the small-diameter opening. Some embodiments may further include fluid level markings on a side of the barrel portion for measuring an amount of the expressed colostrum.

In another aspect, a system for collecting colostrum from a breast of a human and dispensing the colostrum to a newborn may include a colostrum collection funnel and a syringe. The colostrum collection funnel may include a wide proximal portion for facilitating collection of expressed colostrum, a narrow distal portion opposite the wide proximal end and having at least one connection member, and a cone-shaped middle portion between the proximal and distal portions, wherein a wall of the cone-shaped portion is straight. The syringe is removably attachable with the connection member of the narrow portion of the colostrum collection funnel. In some embodiments, the wide proximal portion of the colostrum collection funnel curves outward from the cone-shaped middle portion. Optionally, the funnel may include multiple, longitudinal ribs on an outer surface of the middle portion, for facilitating holding the funnel.

Other and further aspects and features will be evident from reading the following detailed description of the embodiments.

BRIEF DESCRIPTION OF DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments illustrated in the accompanying drawings and other embodiments is provided further below. These drawings depict only typical embodiments and should not, therefore, be considered limiting of the scope of the claims.

FIG. 1 is a perspective view of a device for collecting and administering colostrum/milk, in accordance with some embodiments;

FIG. 2 is a side view of the device of FIG. 1;

FIG. 3 is a side cross sectional view of the device of FIG. 1;

FIGS. 23A-23G are perspective, top, side, side, cross-sectional, bottom and cross-sectional views, respectively, of an alternative embodiment of a colostrum collection device.

DETAILED DESCRIPTION

Figure 4:
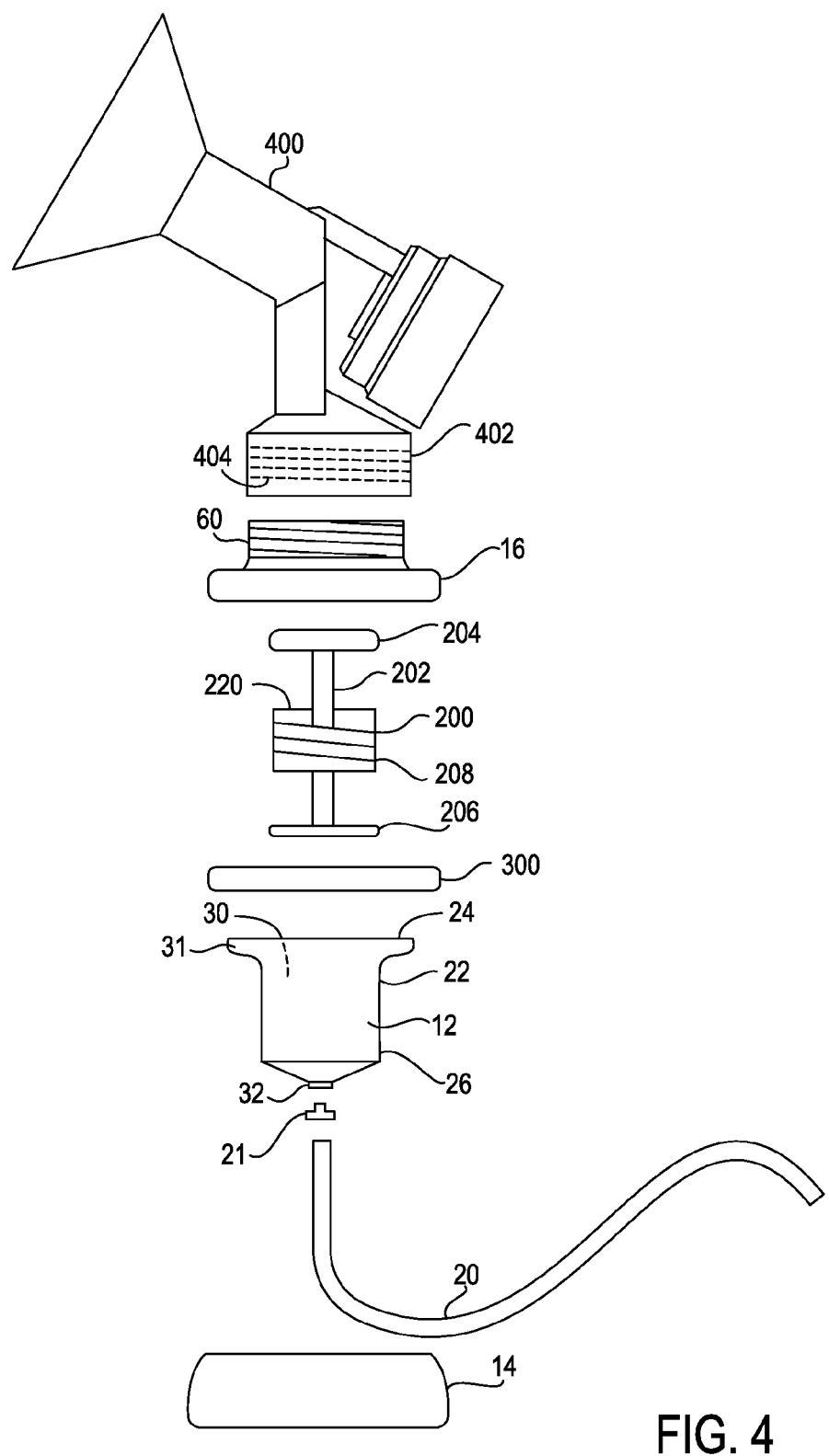
FIG. 4 is an exploded view of the device of FIG. 1, particularly showing the device being used with a pump.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

FIG. 1 is a perspective view of a device 10 for collecting and administering colostrum in accordance with some embodiments. FIG. 2 is a side view of the device 10, and FIG. 3 is a side cross sectional view of the device 10. The device 10 will be described with reference to collecting and administering colostrum from a breast. However, in other embodiments, the device 10 may be used to collect and administer mature milk from a breast. Thus, as used in this specification, the term "fluid" is not limited to colostrum, and may refer to mature milk as well.

As shown in FIGS. 1-3, the device 10 includes a container 12, a base 14, a coupler 16, a plunger 18, a tube 20, a blocker 21, and a lid 300. The container 12 has a first end 22 with a first opening 24, a second end 26 with a second opening 28, and a compartment 30 extending from the first end 22 to the second end 26. The first opening 24 is configured to receive colostrum from a breast, the compartment 30 is configured to contain the received colostrum, and the second opening 28 is configured to deliver the colostrum from the compartment 30 to a subject (e.g., an newborn, toddler, etc.).

As shown in FIG. 3, the first end 22 of the container 12 has a lip 31 that surrounds the first opening 24. The lip 31 (and optionally also the rest of the container 12) may be made from a hydrophobic material, which allows fluid to slide along the surface of the lip 31 (and the container 12). The lip 31 extends away from an axis of the container 12 in a flare-configuration, and has a curvilinear profile. Such configuration is advantageous because it allows the container 12 to be placed directly against a breast to collect breast fluid using hand expression, wherein the lip 31 prevents or reduces the risk of spillage, and the curvature of the lip 31 allows the breast fluid to "slide" to the bottom of the container 12. Furthermore, the lip 31 provides a ledge that allows a user to hold the container 12 by placing fingers underneath it. In addition, the lip 31 may have a profile that is designed for efficient cup feeding. In other embodiments, the lip 31 may have other configurations. For example, in other embodiments, the lip 31 may have a funnel shape, and/or a rectilinear configuration. Also, in other embodiments, the lip 31 is optional, and the container 12 may not include any lip at the first end 22 of the container 12.

In the illustrated embodiments, the second end 26 of the container 12 has a protrusion 32 that defines the second opening 28. During use, when the container 12 is used to collect colostrum from a breast, the blocker 21 may be detachably coupled to the protrusion 32 that that it covers the second opening 28. For example, the blocker 21 may be configured (e.g., sized and/or shaped) to be inserted into the second opening 28 so that the blocker 21 is frictionally engaged with an interior surface of the protrusion 32. Alternatively, the blocker 21 may be configured (e.g., sized and/or shaped) to be placed around the protrusion 32 so that the blocker 21 frictionally engages with an exterior surface of the protrusion 32. When the blocker 21 is detachably coupled to the second end 26 of the container 12, it prevents fluid in the container 12 from exiting through the second opening 28 at the second end 26 of the container 12. It should be noted that the manner in which the blocker 21 is detachably coupled to the container 12 is not limited to the example discussed previously and that blocker 21 may be detachably coupled to the container 12 in other configurations. For example, in other embodiments, the blocker 21 may include a connector for detachably coupling to the second end 26 of the container 12. For example, the connector may include threads that are configured to threadingly engage with corresponding threads at the protrusion 32 (either at an exterior surface of the protrusion 32, or an interior surface of the protrusion 32) of the container 12. Furthermore, in other embodiments, the protrusion 32 is optional, and the container 12 may not include the protrusion 32. In such cases, the blocker 21 may be coupled to the container 12 by inserting the blocker 21 into the second opening 28 at a bottom surface of the container 12. Also, in other embodiments, the device 10 may further include a member (not shown) that connects the blocker 21 to the container 12. The member may have one end connected to the blocker 21, and another end connected to the container. The member prevents the blocker 21 from being separated from the container 12 even when the blocker 21 is not inserted into the second opening 28, thereby preventing the blocker 21 from getting lost.

After fluid has been collected inside the container 12, the blocker 21 may be removed from the container 12, and a first end 40 of the tube 20 may be detachably coupled to the second end 26 of the container 12 by inserting the first end 40 of the tube 20 into the second opening 28, so that the tube 20 is detachably coupled to the container 12 using friction. When the tube 20 is coupled to the container 12, a lumen in the tube 20 is in fluid communication with the second opening 28. A second end 42 of the tube 20 may be placed into a mouth of the subject. The tube 20 then functions as a feeding tube for delivering colostrum from the container 12 to the subject. In some embodiments, the tube 20 may be a 5 French feeding tube. In other embodiments, the tube 20 may have other dimensions.

In other embodiments, the tube 20 is optional, and the device 10 may not include the tube 20. In such cases, the protrusion 32 at the second end 26 of the container 12 may be placed directly into a mouth of the subject for administering the colostrum to the subject. It should be noted that the manner in which the tube 20 is detachably coupled to the container 12 is not limited to the example discussed previously, and that tube 20 may be detachably coupled to the container 12 in other configurations. For example, in other embodiments, the tube 20 may be configured (e.g., sized and/or shaped) so that it is placed around the protrusion 32 at the second end 26 of the container 12, and is detachably secured to the container using friction. Also, in other embodiments, the first end 40 of the tube 20 may include a connector for detachably coupling to the second end 26 of the container 12. For example, the connector may include threads that are configured to threadingly engage with corresponding threads at the protrusion 32 (either at an exterior surface of the protrusion 32, or an interior surface of the protrusion 32) of the container 12. Furthermore, in other embodiments, the protrusion 32 is optional, and the container 12 may not include the protrusion 32. In such cases, the first end 40 of the tube 20 may be coupled to the container 12 by inserting the first end 40 into the second opening 28 at the bottom surface of the container 12.

As shown in FIG. 3, the base 14 has a recess 50 with a first recess portion 52 configured (e.g., sized and/or shaped) to accommodate the second end 26 of the container 12, and a second recess portion 54 that is smaller than the first recess portion 52. The second recess portion 54 is configured to accommodate the protrusion 32 of the container 12. The base 14 allows the container 12 to be supported in a vertical position when the container 12 is not being used.

In the illustrated embodiments, the coupler 16 has a ring configuration, and includes threads 60 at an exterior surface 62 of the coupler 16. The coupler 16 is configured to detachably couple to the first end 22 of the container 12 during use. As shown in the illustrated embodiments, the coupler 16 has a latch that extends circumferentially around the coupler 16, which allows the coupler 16 to detachably couple to the lip 31 of the container by a snap-fit connection. When the coupler 16 is coupled to the container 12, the coupler 16 may be used to detachably couple to a pump connector of a pump system, so that the pump system may be used to collect fluid (e.g., colostrum, milk) from a breast, and deliver the fluid into the container 12. FIG. 4 illustrates a suction cup 400 which is a part of the pump system (not shown) that is configured to provide suction through the suction cup (pump flange) 400 to express or extract fluid from within the breast, wherein the pump system may be a manually actuated pump or an electric pump. In some cases, the suction cup 400 may be any of the breast shields (or "pump flanges") manufactured by Medela, Inc., Ameda, Inc., Evenflo Company, Inc., or other manufacturers. In other embodiments, the suction cup 400 may be provided by other manufacturers, or may be provided by a manufacturer of the device 10. Also, in some embodiments, the suction cup 400 may be considered to be a part of the device 10. The suction cup 400 includes a connector 402 with threads 404 that threadingly engage with the threads 60 at the exterior surface 62 of the coupler 16. In the case in which the suction cup 400 is provided by a different manufacturer from that of the device 10, wherein the suction cup 400 is configured to detachably couple to a baby bottle, the coupler 16 may be configured so that it can mate with the connector 402 of the suction cup 400, thereby allowing the container 12 to be used in place of the baby bottle. In particular, the coupler 16 may have an exterior dimension that allows the portion with the threads 60 to be inserted into the connector 402, and the threads 60 may have a pitch and dimension that allows the threads 60 to fittingly engage with the threads 404 at the connector 402. The coupler 16 may be made from silicone, polypropylene, other suitable materials, or any combination thereof, in different embodiments. Also, in some cases, different parts of the coupler 16 may be made from different materials having different stiffness. For example, in some embodiments, the top part of the coupler 16 may be made from a first material (e.g., polypropylene) that is stiffer than a second material (e.g., silicone) from which the bottom part of the coupler 16 is made.

As shown in FIGS. 3 and 4, the plunger 18 has a coupler 200, a shaft 202 extending through the coupler 200, a manual actuator 204 attached to one end of the shaft 202, and a plunger head 206 attached to another end of the shaft 202. The coupler 200 includes two or more tabs 220, which allows a user to turn the coupler 200. The shaft 202 is slidably coupled to the coupler 200 so that the plunger head 206 may be advanced towards a base of the container 12 by pressing the actuator 204 relative to the coupler 200, or may be retracted away from the base of the container 12 by pulling the actuator 204 relative to the coupler 200. As shown in the illustrated embodiments, the coupler 200 of the plunger 18 has threads 208 at an exterior surface of the coupler 200. The threads 208 of the coupler 200 are configured to mate with threads 64 at an interior surface 66 of the coupler 16.

In other embodiments, instead of providing the tabs 220 for turning the coupler 200, the plunger 18 may have other mechanisms for turning the coupler 200. For example, in other embodiments, the shaft 202 of the plunger 18 may have a groove that slidingly mates with a protrusion at an interior surface of the coupler 200. Such configuration allows the shaft 202 to slidingly move relative to the coupler 200 along a longitudinal axis of the shaft 202, while also allowing the coupler 200 to be turned about the longitudinal axis of the shaft 202 by turning the actuator 204 about the longitudinal axis of the shaft 202.

During use, the plunger 18 may be detachably coupled to the container 12. In particular, the coupler 16 may be used to couple the plunger 18 to the container 12 by detachably securing the lip 31 of the container 12 to the circumferential latch of the coupler 16 via the snap-fit connection, and by detachably securing the plunger 18 to the top portion of the coupler 16 using the threads 208 and 64 (i.e., by turning the coupler 200 of the plunger 18 relative to the coupler 16 using the tabs 220). The actuator 204 may then be used to advance the plunger head 206 inside the compartment 30 of the container 12 to push fluid out of the second opening 28 at the second end 26 of the container 12.

It should be noted that the manner in which the plunger 18 is coupled to the container 12 is not limited to the embodiments described. In other embodiments, the plunger 18 may be directly or indirectly coupled to the container 12 using other mechanisms. For example, in other embodiments, the coupler 200 of the plunger 18 may be screwed into the container 12, having corresponding threads at an interior surface of the container 12 at the first end 22. In further embodiments, the coupler 200 of the plunger 18 may not have threads 60. Instead, the coupler 200 of the plunger 18 may be configured to secure itself directly to the container 12 using a snap-fit connection, a frictional engagement, or any of other types of connection. In still further embodiments, the coupler 200 of the plunger 18 may be configured to secure itself directly to the coupler 16 (and indirectly to the container 12) using a snap-fit connection, a frictional engagement, or other types of connection.

Figure 7:
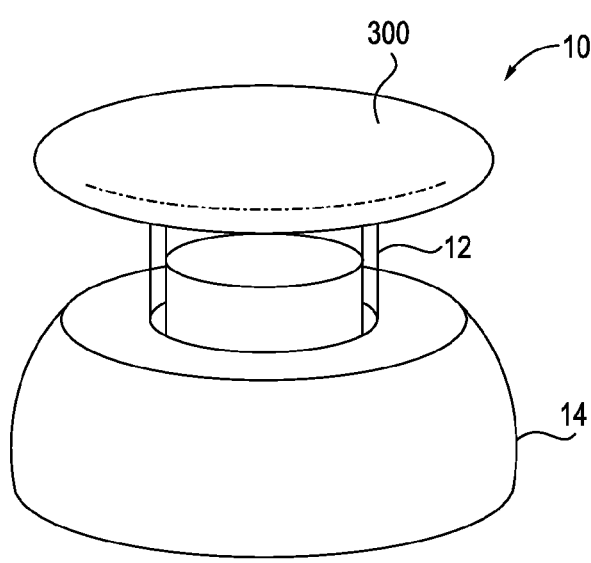
FIG. 7 illustrates the device of FIG. 6, particularly showing the container with a lip coupled thereto.

As shown in FIGS. 1, 4, and 7, the lid 300 of the device 10 is configured for covering the first opening 24 of the container 12. The lid may be made from silicone, a polymer, or other suitable material(s). The lid 300 is useful when the coupler 16 and the plunger 18 are not coupled to the container 12 and when the user wishes to transport the collected fluid in the container 12. In such cases, the lid 300 may be detachably coupled to the first end 22 of the container 12. The lid 300 includes a latch that extends circumferentially around the lid 300 (as similarly discussed with reference to the coupler 16). The latch allows the lid 300 to detachably couple to the lip 31 of the container 12 using a snap-fit connection. In the illustrated embodiments, the lid 300 is configured (e.g., sized, shaped, etc.) to detachably couple to the container 12. In other embodiments, the lid 300 may be configured to detachably couple to the coupler 16. Also, in other embodiments, the lid 300 may be configured to detachably couple to the container 12/coupler 16 using other mechanisms other than a snap-fit mechanism. For example, in other embodiments, the lid 300 may be configured to detachably couple to the container 12/coupler 16 using screw threads, clip(s), friction, etc.

Figure 5:
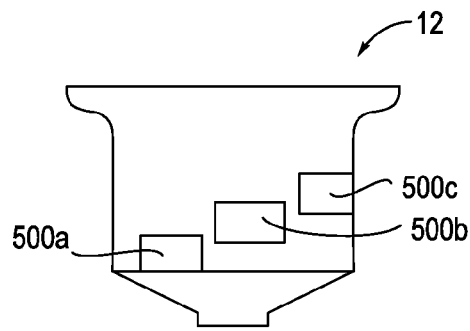
FIG. 5 illustrates the container of FIG. 1, particularly showing the container having multiple markings in accordance with some embodiments.

In any of the embodiments described herein, the container 12 may include one or more markings for indicating target fluid level(s). FIG. 5 illustrates the container 12, particularly showing the container 12 having multiple markings 500a-500c in accordance with some embodiments. The first marking 500a indicates a first range (e.g., 2-10 ml) of desired fluid volume in the first day (day 1) after childbirth, the second marking 500b indicates a second range (e.g., 5-15 ml) of desired fluid volume in the second day (day 2) after childbirth, and the third marking 500c indicates a third range (e.g., 15-30 ml) of desired fluid volume in the third day (day 3) after childbirth. The ranges are illustrated as having overlapping regions. In other embodiments, two adjacent ranges may not be overlapping. Also, in further embodiments, the three ranges of volumes may be different from the examples mentioned. In some embodiments, the markings 500a-500c may be molded during the manufacturing of the container 12. In other embodiments, the markings 500a-500c on the container 12 may be color-coded, wherein different colors represent different respective ranges of target fluid volume. The markings 500a-500c are advantageous, because they allow a user of the device 10 to gauge how much fluid should be collected from the breast.

In the above embodiments, the markings 500a-500c represent different respective ranges of target volume. In other embodiments, the markings 500a-500c may represent different target volume levels (i.e., instead of ranges of levels). Also, in the above embodiments, the markings 500a-500c indicate different respective ranges of fluid volume desired to be collected in different days after childbirth. In other embodiments, instead of "day(s)" after childbirth, the markings 500a-500c may correspond with different hour(s) after birth, number of meals, or other units that correspond with passage of time. In further embodiments, instead of three markings 500a-500c, the container 12 may include less than three markings or more than three markings. Also, in other embodiments, instead of, or in addition to, the configuration shown, the markings 500a-500c may include numerical information on the container 12, such as volume levels (e.g., in unit of ml, cc, etc.), "1" in the region for marking 500a, "2" in the region for marking 500b, and "3" in the region for marking 500c.

In any of the embodiments described herein, any of the components of the device 10 may be made from a suitable polymer, plastic, silicone, other materials, or combination thereof. In some cases, any components of the device 10 (e.g., the container 12, plunger 18, lid 300) that may potentially come into contact with breast fluid may be made from a BPA-free material.

Also, in any of the embodiments, the container 12 may have a size that is smaller than a size of a baby bottle. For example, in any of the embodiments described herein, the container 12 may have a total height that is anywhere between 0.5 inch and 3 inches, and more preferably, between 1 inch and 2 inches (e.g., 1.5 inch). Also, in some embodiments, the container 12 may be configured to hold at most 40 ml of fluid, and more preferably, at most 30 ml of fluid, or less. Such size feature is advantageous, because the amount of colostrum produced by a mother may not be significant, and if a large container (e.g., a baby bottle) is used to collect the colostrum, a mother may be discouraged from breastfeeding when she sees that there is very little colostrum relative to the size of the container. Thus, providing a container 12 that is smaller than a size of a baby bottle has functional reasons, and is not a matter of design choice. FIG. 3 provides some exemplary dimensions (in unit of inch) for the device 10 in accordance with some embodiments. In other embodiments, the container 12 may have other dimensions that are different from those described.

A method of using the device 10 in accordance with some embodiments will now be described. First, to set up the device 10 for collecting breast fluid (e.g., colostrum, milk), the plunger 18 is separated from the container 12 by turning the coupler 200 of the plunger 18 relative to the coupler 16 (e.g., using the tabs 220) until the threads 208 and 64 are decoupled from each other. The coupler 16 is detachably coupled to the first end 22 of the container 12 by snap-fitting the edge of the coupler 16 against the lip 31 of the container 12, and the suction cup 400 of a pump system is detachably coupled to the coupler 16 by screwing the coupler 16 relative to the connector 402 of the suction cup 400. Thus, the suction cup 400 is secured to the container 12 through the coupler 16. The blocker 21 is then used to cover the second opening 28 at the second end 26 of the container 12. The suction cup 400 is placed over the breast, and the pump system is then activated to create suction at the suction cup 400, thereby expressing or extracting breast fluid out of the holes in the nipple at the breast. The collected breast fluid enters the container 12 through the first opening 24 at the first end 22 of the container 12, and is contained in the compartment 30 of the container 12.

Figure 6:
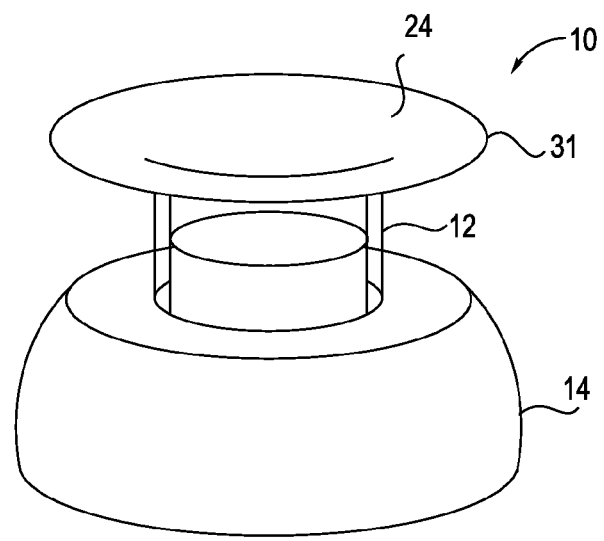
FIG. 6 illustrates the device of FIG. 1, particularly showing the container with the coupler and plunger removed.

In other embodiments, instead of using a pump system to collect the colostrum/milk, hand expression may be employed to collect the colostrum/milk. In such cases, the coupler 16 may be removed from the container 12 (FIG. 6). The first end 22 of the container 12 is then placed below a nipple, so that fluid exiting from the nipple resulting from hand expression may be collected by the container 12.

After the breast fluid has been collected, the suction cup 400 is detached from the coupler 16. If hand expression was used to collect the breast fluid, the coupler 16 is then detachably coupled to the container 12. The plunger 18 is then detachably coupled to the first end 22 of the container 12 through the coupler 16. In particular, the plunger 18 is inserted into the top portion of the coupler 16, and is turned using the tabs 220 to threadingly engage the threads 208 at the plunger 18 against the threads 64 at the interior surface 66 of the coupler 16. After the plunger 18 is mounted, the plunger head 206 functions as a seal to prevent the collected breast fluid in the container 12 from leaking out of the first opening 24 of the container 12. With both the first and second openings 24, 28 covered and sealed, the container 12 may then be used to transport the collected breast fluid from the mother to a subject.

Alternatively, instead of using the plunger 18 to seal the first end 22 of the container 12, the lid 300 may be used to cover the first opening 24 at the first end 22 of the container 12. In such cases, the coupler 16 is not coupled to the container. Instead, the lid 300 is snap-fit against the lip 31 of the container 12 to thereby seal the first opening 24 at the container 12 (FIG. 7). The container 12 may then be used to transport the collected breast fluid from the mother to a subject.

In some cases, when a nurse or a personnel at a hospital is not ready to transport the collected breast fluid, or when the mother wishes to collect more breast fluid before the container 12 is delivered to the subject, the second end 26 of the container 12 may be placed into the recess 50 of the base 14, and the container 12 may be vertically supported by the base 14.

Once delivered to the subject, the container 12 with the breast fluid may then be used to feed the subject. If the plunger 18 is already coupled to the container 12, the container 12 may then be turned upside down, and the blocker 21 is then removed from the second end 26 of the container 12. On the other hand, if the plunger 18 is not already coupled to the container 12 (i.e., if the lid 300 is on the container), the lid 300 may first be removed from the container 12, and then the coupler 16 and the plunger 18 may be coupled to the container 12.

In some embodiments, the protrusion 32 at the second end 26 of the container 12 may be placed into the subject's mouth. The user of the device 10 may then advance the plunger head 206 inside the container 12 by pressing on the actuator 204 of the plunger 18, thereby pushing the breast fluid out of the second opening 28 and into the subject's mouth. In other embodiments, the first end 40 of the feeding tube 20 may be detachably coupled to the second end 26 of the container 12, and the second end 42 of the feeding tube 20 may be placed inside the subject's mouth. The user of the device 10 may then advance the plunger head 206 inside the container 12 by pressing on the actuator 204 of the plunger 18, thereby pushing the breast fluid out of the second opening 28, into the feeding tube 20, and into the subject's mouth.

When the feeding is completed, or if the person feeding the subject wishes to temporarily stop the feeding, the second opening 28 of the container 12 may be closed by using the blocker 21, and the container 12 may be vertically supported by the base 14. In some embodiments, the device 10 includes one base 14, in which cases, when the container 12 is being delivered from the mother to the subject, the base 14 may also be delivered together with the container 12 so that the person feeding the subject may use the base 14 to support the container 12 if desired. In other embodiments, the device 10 may include two bases 14. In such cases, one base 14 may stay with the mother so that she can use the base 14 to support the container 12, and the other base 14 may stay with personnel at the hospital so that the personnel feeding the subject can use the base 14 to support the container 12.

In some embodiments, all of the components of the device 10 are for a single use. In other embodiments, any one or more of the components (such as the base 14) of the device 10 may be for multiple use.

As illustrated in the above embodiments, the device 10 is advantageous because the same device 10 may be used for collecting colostrum/milk, storing the colostrum/milk, transporting the colostrum/milk, and administering the colostrum/milk to a subject. Thus, the device 10 obviates the need to transfer colostrum/milk from a medicine cup, spoon, pump bottle, or other containers, to another container for administering the fluid to the subject. The device 10 is also advantageous, because it provides two modes of breast fluid collection, wherein in the first mode, the device 10 is detachably coupled to a pump system to receive breast fluid from the pump system, and in the second mode, the device 10 is not detachably coupled to any pump system, but is placed directly next to a breast for collecting breast fluid resulted from hand expression. The device 10 promotes feeding the newborn with human colostrum/milk, which in turn may result in lower health care costs, and many other benefits.

Although embodiments of the device 10 have been described with reference to the device 10 having the coupler 16, in other embodiments, the coupler 16 is optional, and the device 10 may not include the coupler 16. In such cases, instead of using a pump system to collect colostrum/milk into the container 12, the colostrum/milk may be collected into the container 12 manually by using hand expression. After the breast fluid has been collected into the container 12, the plunger 18 may then be inserted into the compartment 30 of the container 12 to push the fluid out of the second opening 28 of the container 12.

In still further embodiments, the device 10 may include the coupler 16, but the coupler does not include the threads 60 or any other mechanism for coupling to a pump connector. In such cases, instead of using a pump system to collect colostrum/milk into the container 12, the colostrum/milk may be collected into the container 12 manually by using hand expression. After the breast fluid has been collected into the container 12, the coupler 16 may then be used to detachably couple the plunger 18 to the first end 22 of the container, as similarly discussed. The plunger 18 may then be used to push the fluid out of the second opening 28 of the container 12.

Figure 8:
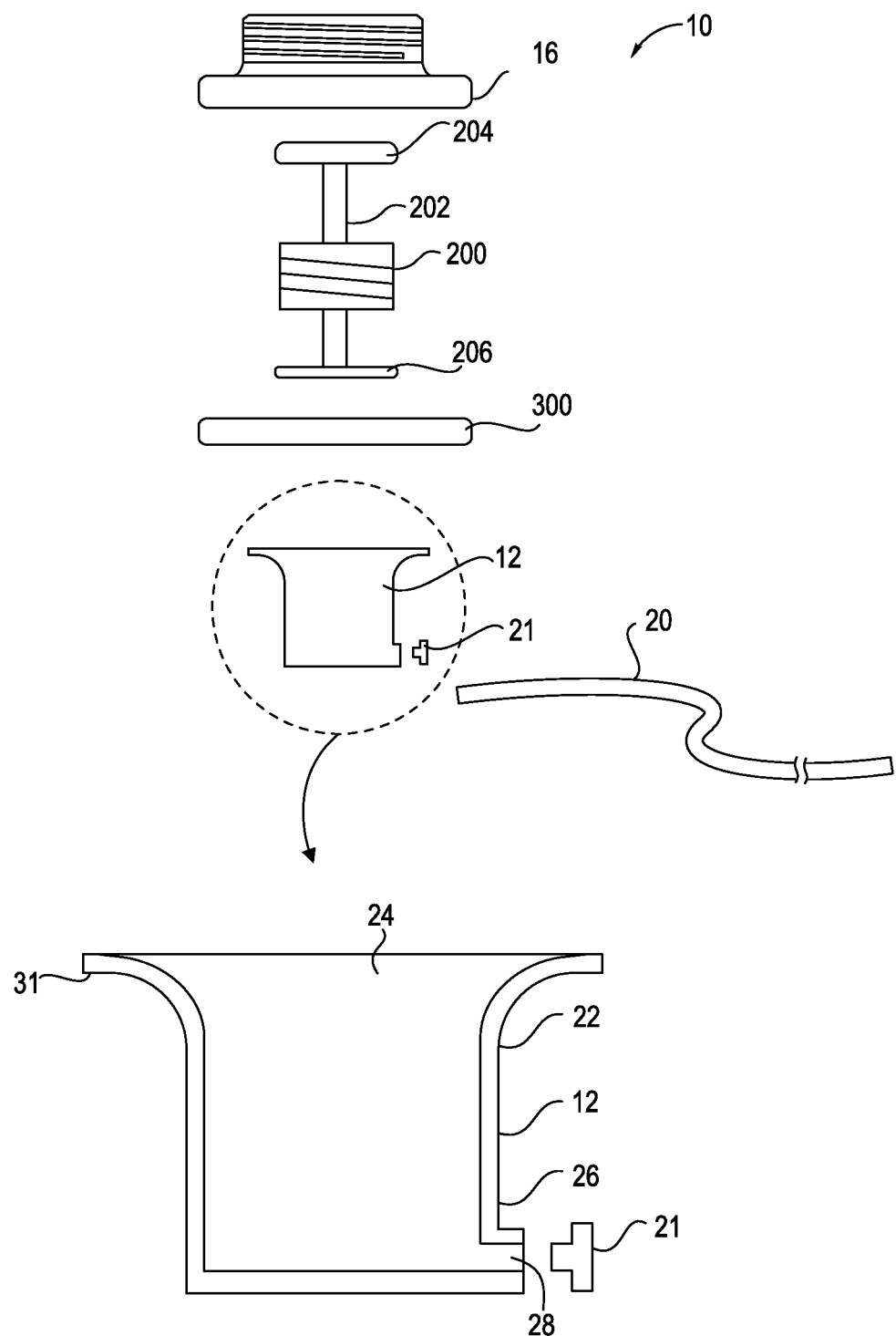
FIG. 8 illustrates another device for collecting and administering colostrum/milk, in accordance with an alternative embodiment.

In the above embodiments, the second opening 28 has been illustrated as being at the bottom surface of the container 12. In other embodiments, the second opening 28 may be implemented at other locations on the container 12. For example, in other embodiments, the second opening 28 may be implemented at a side of the container 12 (FIG. 8). Such configuration obviates the need to have the base 14, and the container 12 may be directly placed on a flat surface. Also, in further embodiments, instead of having a protrusion that sticks out from a side of the container 12, as illustrated in the figure, the container 12 may not have the protrusion. In such cases, the second opening 28 may be implemented at a side wall of the container 12.

Also, in further embodiments, the plunger 18 may be at other locations. For example in other embodiments, the container 12 may include a side opening at the side wall of the container 12 that is configured to allow an insertion of the plunger 18. In such cases, while the first opening 24 of the container 12 is being used to collect colostrum/milk, the plunger 18 may remain coupled to the side of the container 12. After the colostrum/milk is collected into the container 12, the lid 300 may be used to cover the first opening 24, or the top of the coupler 16 (if the coupler 16 is already coupled to the container 12). The blocker 21 is then removed from the second opening 28 of the container 12. The plunger 18 at the side of the container 12 may then be actuated to push the collected colostrum/milk out of the second opening 28, either directly from the second opening 28 into a subject's mouth, or from the second opening 28 into a feeding tube.

Figure 9:
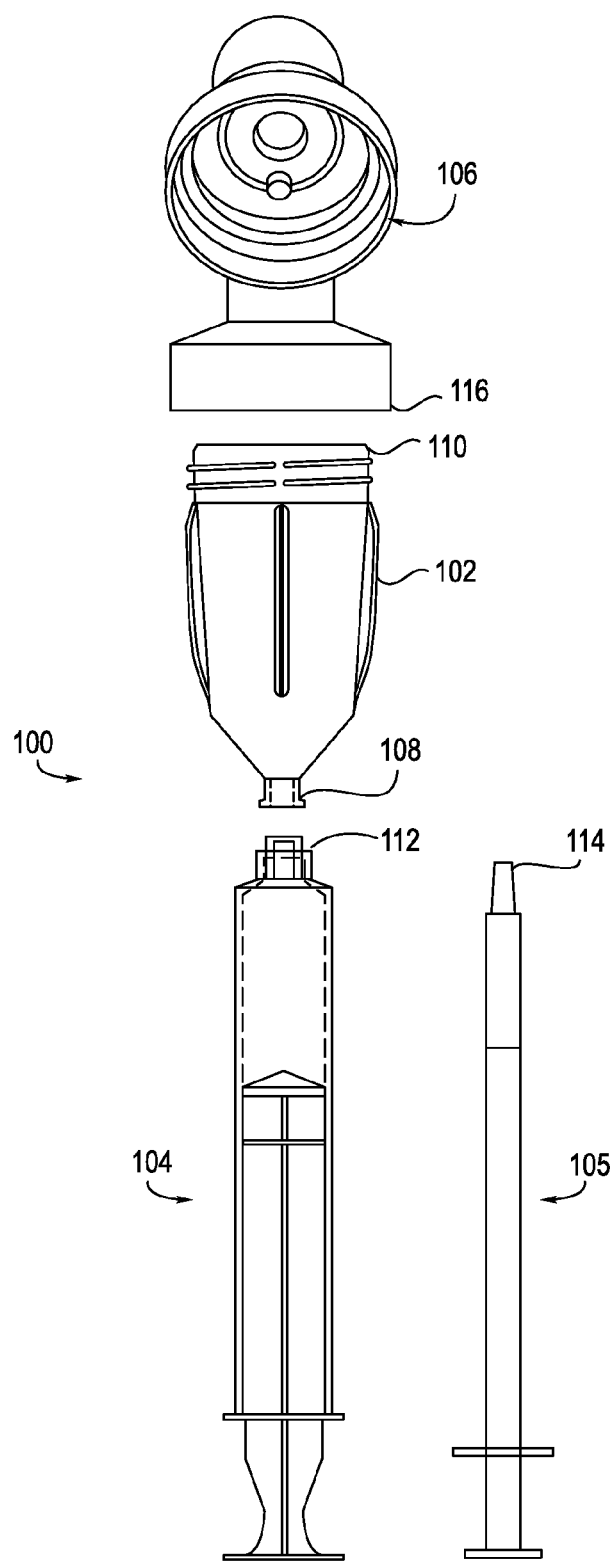
FIG. 9 is an exploded view of a system for collecting and administering colostrum/milk, in accordance with another alternative embodiment.

Referring now to FIG. 9, in an alternative embodiment, a colostrum collection and dispensing system 100 may suitably include an adapter 102, one or more collection/suction vessels 104, 105 (or "suction members"—i.e., "syringes" in the embodiment illustrated in FIG. 9), and an interface 106 for acting as a conduit of colostrum into the suction members 104, 105. In some embodiments, the system 100 may also include a tube (not shown), which may be referred to as a feeding tube, for attaching to one of the suction members 104, 105 and advancing into an newborn's mouth or nostril for facilitating dispensing the collected colostrum to the newborn.

In any given embodiment, the system 100 may include a smaller subset of the components shown in FIG. 9 or may include additional components not pictured. For example, in some embodiments, the system 100 may simply include multiple adapters 102, such as three or four adapters 102 housed within an outer package and also optionally housed in individual packages. Each adapter 102 may be used by a woman for one day during the first 3-4 days after childbirth. In these embodiments, the adapters 102 may be used with off-the-shelve interfaces 106, such as currently available breast shields from companies such as Medela, Inc. These interfaces 106 may be used with any suitable breast pump system. The adapters 102 may also be used with one or more off-the-shelf syringes 104, 105, feeding tubes (not shown), and/or the like. In other embodiments, the system 100 may include all the components shown in FIG. 9. Therefore, the embodiment shown in FIG. 9 should not be interpreted as limiting the type and/or number of components that may be provided with the system 100.

In use, the adapter 102 attaches at a first end 108 to an end 112, 114 of one of the syringes 104, 105 and at an opposite, second end 110 to an end of the interface 106. Once the system is coupled together, the user may then contact the interface 106 with the breast and apply suction force via the syringe 104, 105, a breast pump connected to the interface 106, or both. Typically, using the system 100 as illustrated in FIG. 9, the interface FIG. 9, the interface 106 (or "breast shield" in this embodiment) is attached to a breast pump system, which mechanically helps to express colostrum into the interface 106. The suction member (syringe 104 or 105) may then be used to draw colostrum through the interface 106 and adapter 102 into the syringe 104, 105. Because the syringes 104, 105 may generate at least some suction force, they are referred to generally herein as "suction members." However, the syringes 104, 105 are only one example of a variety of different types of possible suction members, as will be described further below. The syringe 104, 105 may then be used to contain the colostrum for as short a time as just a few moments to as long as the colostrum can be kept fresh. In some embodiments, the user may remove the adapter 102 from the syringe 104, 105 and immediately place the end of the syringe 104, 105 into the newborn's mouth for dispensing the colostrum. In other embodiments, a flexible tube may be attached to one end of the syringe 104, 105, and the tube may be used to pass colostrum through the newborn's mouth or nose to the throat. In other embodiments, the syringe 104, 105 containing colostrum may be stored, for example in a refrigerated compartment, for later use.

One important feature of the system 100 is that colostrum is collected into a predominantly closed receptacle (i.e., one of the syringes 104, 105 in the embodiment of FIG. 9), and that same receptacle is used to administer the colostrum to the newborn. Since the colostrum is collected directly into a syringe 104, 105, the method for extracting and delivering colostrum is simplified by eliminating the step of transferring the colostrum from a collection receptacle into a feeding syringe. The system 100, as well as other system embodiments described below, may be referred to herein as a "connected system." This simply means that at least some component parts of the system are attachable to one another during at least part of the colostrum collection and dispensing process. For example, in the embodiment of FIG. 9, the adapter 102 is connectable to the syringe 104, 105 at one end and to the interface 106 at the other end. Thus, the system 100 is "connected," at least during collection of colostrum from the breast. The system 100 then becomes detached for dispensing the colostrum to the newborn. In some cases, the dispensing step may involve connecting another system component (i.e., a tube) to the syringe 104, 105. This connected system is in contrast to the commonly used methods for collecting and dispensing colostrum, in which the colostrum is expressed into an open cup, bottle or other container, and then a separate syringe or other device is used to pull the colostrum out of the container and feed it to the newborn. Using a "connected system," as described in the present application, not only simplifies the process of extracting and administering colostrum, but it will also likely help to reduce infections and passage of harmful germs, since the colostrum is drawn directly into the suction member and then fed directly to the newborn from the suction member.

Another likely advantage of the system 100 and other system embodiments described herein is that they are designed to be less intimidating to the women who use them. For example, the current method of expressing colostrum into a cup, bottle or similar container typically involves the use of a large collection container. The amount of colostrum expressed at one time, however, is almost always very small—just a few milliliters. Women may often become intimidated and discouraged, because the amount of colostrum they express, which is likely a very normal amount, will typically look like almost nothing when housed in a large collection vessel. By contrast, the system 100 uses relatively small-volume syringes 104, 105 (or other small-volume suction members in other embodiments). In the example shown in FIG. 9, for example, the syringes are a 5 mL syringe 104 and 1 mL syringe 105. These small volumes make it less intimidating for a woman trying to express colostrum from her breast, compared to the current, typical practice of trying to express colostrum into a large cup or bottle.

In various embodiments, the interface 106 may allow suction force, mechanical force, oscillation force, electric stimulation, other force(s) or combinations thereof to be transmitted to the breast. The interface 106 also simultaneously serves as a conduit for colostrum collection. The interface 106 may have a shape of a funnel, bulb, dome, or any other suitable shape, and is sufficiently flexible to allow for maximal apposition or partial apposition with breast tissue to reduce dead volume and thus minimize colostrum loss. The interface may cover all or part of the nipple, areola or breast, and may or may not allow for manual expression or other colostrum expression techniques to be applied simultaneously. In some embodiments, ridges, grooves, bumps, regions of hydrophobic and hydrophilic coatings to guide material, electro-responsive strips, and/or other structures may be added to the internal surface of the interface 106 to serve as flow channels for colostrum. The internal volume of the interface 106 is configured to minimize wasted colostrum during the collection process.

The interface 106 connects to the collection/suction vessel 104, 105 in a detachable manner. This detachable interface 106 may include one or more components that are flexible, such as a tube or ridged such as a L shape bend, T connector, or other connection configuration such that the colostrum may flow from the collection area into a container such as a syringe, vial, cartridge, or other containment vessel for the colostrum. Such detachable connection may be achieved in a screw-on manner, through a Luer connection, click connector, pin connector, cone and socket, magnetic link, stopcock valve connector, squishing valve, or other standard or unique connection mechanism. In addition, the sizing of the connector may be such that standard interfaces may be used with the collection/suction vessel 104, 105, or the interface 106 may be used with standard collection vessels and suction mechanisms. The connector mechanism may be an independent component with one or multiple connection ports, or may be achieved through design features of the interface and collection/suction member 104, 105. This may be achieved, for example, by the interface 106 having threading at the base of its interior surface, and the collection/suction member 104, 105. Any embodiment of a valve may be included, in various embodiments, to facilitate temporary or long term separation of the collection/suction member 104, 105 and the interface 106. Multi-directional valves may also be contemplated, to allow for colostrum diversion to alternate collection vessels or to provide additional suction force or any mechanism to otherwise alter pressure, volume or contents of the collection/suction member 104, 105 or interface 106.

In some embodiments, such as the one illustrated in FIG. 9, the collection/suction vessel 104, 105 may be a syringe, which may be a standard medical syringe, cartridge, vial, or a uniquely designed syringe. In an alternative embodiment, a collection/suction vessel may be a flexible bulb suction device, which generates a suction force when released from compression. The bulb suction may be used to generate suction force after attachment to the interface 106 to guide fluid from the breast into the bulb as the collection vessel. In other alternative embodiments, the collection/suction vessel 104, 105 may be any other geometric shape with one or more components in which the volume of the vessel is altered in order to alter the internal pressure and/or volume altered to change the dimensions of the vessel in such that the volume of the vessel is not too large for the small volume of colostrum such that material loss or significant adhesion to the surface could possibly occur.

The collection/suction vessel 104, 105 (syringe or other embodiment) may optionally include one of a number of suitable coatings to reduce adherence and/or facilitate collection of colostrum, milk, and or its components, such as but not limited to antibodies. The syringe 104, 105 may be constructed with antibacterial properties and may be constructed of a material that allows for the colostrum to undergo processes such as pasteurization. The syringe plunger may have a locking mechanism to maintain the plunger in such a position to generate a sustained suction force. Additionally, the syringe 104, 105 may have a locking mechanism composed of venting gas, a rotating counterweight, an oscillating spring, and/or other mechanism that oscillates, such that the suction force could be dynamic at least for a period of time. When detached from the interface 106, the collection/suction vessel 104, 105 may be used to dispense the colostrum directly into the mouth, hold the material for storage, or transfer to another vessel. The collection/suction vessel 104, 105 may have a cap to cover the orifice to facilitate storage, reduce potential contamination or spillage concerns and/or facilitate transport once detached from the interface 106. The collection/suction vessel 104, 105 may also optionally include an additional add-on component, such as a nipple piece that may be screwed on to facilitate feeding once the collection/suction vessel 104, 105 has been detached from the interface 106. The collection/suction vessel 104, 105 may also optionally include a component capable of applying cyclic suction force by way of moving the plunger in a repetitive motion and manipulation of a valve, which may or may not be connected to an additional reservoir. Such an effect may be achieved by an electric motor, an oscillating weight that is set at least partially off center to provide a swinging counter weight, a pre-stressed or elastic or spring mechanism designed to release energy in a cyclic fashion once an initial loading force is applied, or other suitable mechanism.

Any of the abovementioned components may be composed of any combination of coated or uncoated paper, plastics, polymer, glass, rubber, biodegradable substances, wax or gels. Any component may be foldable or otherwise pre-stressed, to facilitate storage for transport. Any component may be disposable or reusable. Any component may be composed of a substance that would tolerate traditional sterilization mechanisms, including but not limited to autoclaving, gamma irradiation or ethylene oxide.

Figure 10A:
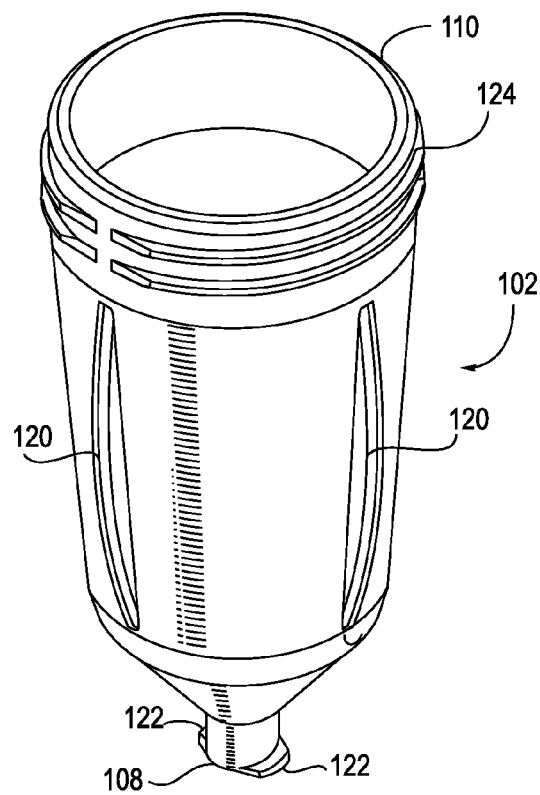
FIGS. 10A and 10B are perspective and side views, respectively, of an adapter of FIG. 9.
Figure 10B:
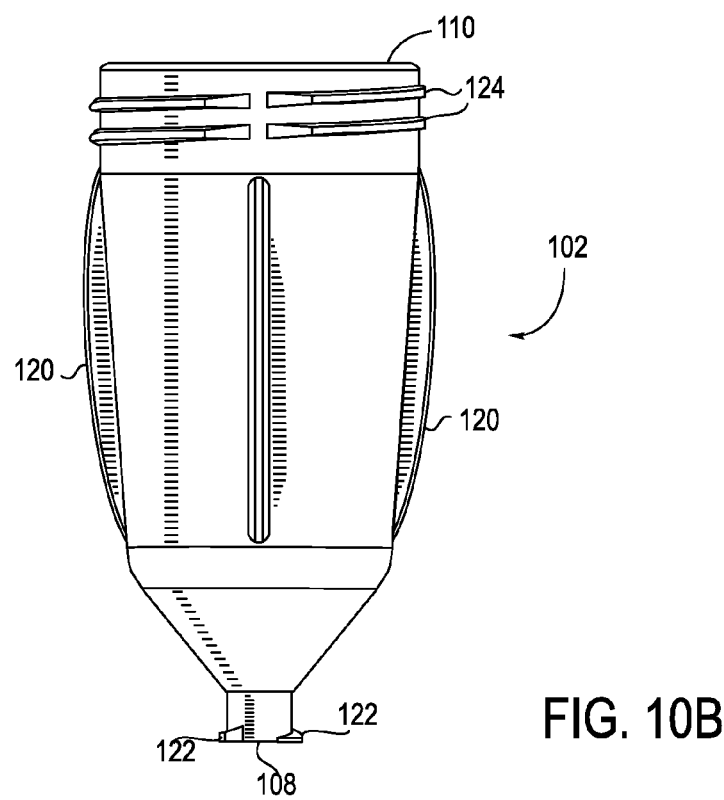

Referring now to FIGS. 10A and 10B, one embodiment of the adapter 102 is illustrated in greater detail. As described previously, the adapter 102 may include the first end 108 for attaching to a suction member, such as a syringe 104, 105, and the second end 110 for attaching to the interface 106. In one embodiment, one or more threads 122 may be included on an outer surface at the first end 108, for engaging with complementary threads on an inner surface of a syringe. For example, in one embodiment, the threads 122 may be compatible/complementary with NuTrio TwistLok™ Enteral Syringes (generic terminology "enteral syringes"), manufactured by Acacia Neonatal, Inc. In other embodiments, the threads 122 may be compatible with other syringes. In some embodiments, multiple different adapters 102 may be available, which are compatible with any of a number of different syringes. For example, a physician, nurse, lactation consultant or the like may be able to provide a woman nursing her newborn with one or more adapters 102, selected from a host of different adapters, based on a type of breast pump system the woman is using. Additional threads 124 may be included on the outer surface of the adapter 102 closer to the second end 110, for engaging with complementary threads on an inner surface of the interface 106. Again, these threads 124 may be designed to be compatible with any suitable interface, such as the breast shields made by Medela, Inc., as referenced above, or any other suitable breast pump shields or other devices. And again, multiple different adapters 102 may be available, each having a different configuration of threads 124. In various alternative embodiments, the first end 108 may not include threads 122. In such embodiments, for example, the first end 108 may fit into the syringe 104, 105 via a press fit. Similarly, in some embodiments, the second end may not include threads 124. Generally, the first end 108 and the second end 110 may fit with complementary syringes 104, 105 and interfaces 106, respectively, via any suitable attachment means Typically, the adapter 102 will be made of plastic and will be disposable. In other embodiments, however, other materials may be used, and it is possible in some embodiments for the adapter 102 to be reusable and capable of being sterilized. In some embodiments, the adapter 102 may include one or more ergonomic features, to facilitate handling and attachment of the adapter 102 to the suction member and the interface 106. For example, in the embodiment shown in FIG. 9, the adapter 102 includes multiple, vertical ridges 120, which may help a user grip and get traction on the adapter 102 when attaching and detaching it. Other possible ergonomic features that might be incorporated into the adapter 102 may include, but are not limited to, overall shape, grooves, horizontal protrusions, diagonal protrusions and bumps.

Figure 11:
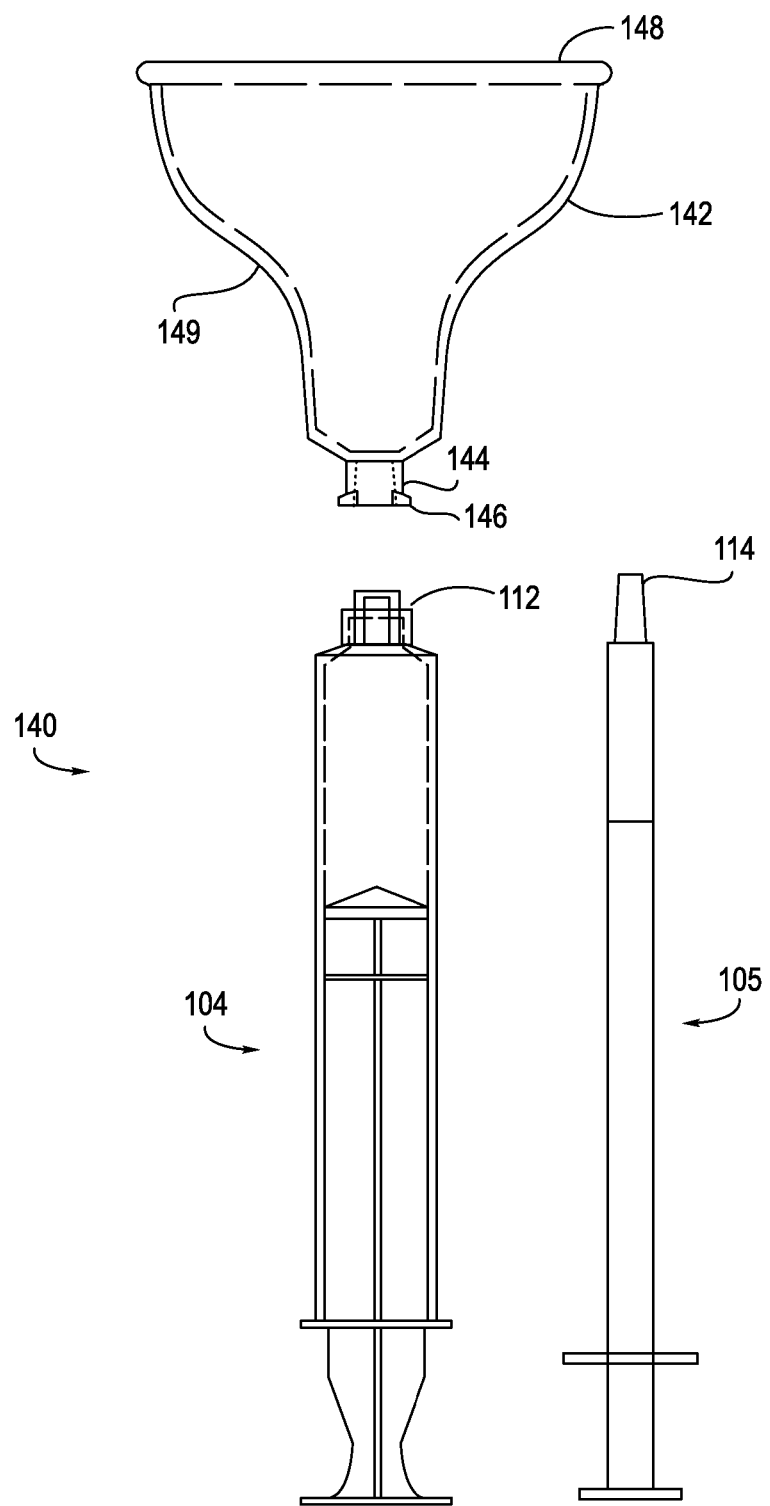
FIG. 11 is an exploded view of a system for collecting and administering colostrum/milk, in accordance with another alternative embodiment.

Referring now to FIG. 11, in another alternative embodiment, a system 140 for collecting colostrum from a breast and dispensing the colostrum to an newborn may include an interface 142 and one or more collection/suction members 104, 105 (again, illustrated here as syringes but other devices possible in alternative embodiments). In this embodiment, the interface 142 has a domed configuration with a flared collection end 148 and a curved surface 149 that tapers down to a narrow distal end and a connector portion 144, which includes one or more threads 146 for connecting to the suction member 104, 105. As in the previously described embodiment, the connector portion 144 is compatible with multiple sizes of suction members 104, 105.

In the embodiment illustrated in FIG. 11, the system 140 does not include an adapter and is not intended to be connected to a breast pump system. Instead, the interface 142 acts as a colostrum collection facilitator. The interface 142 may be flexible or rigid and may be made of any suitable plastic or other material in various embodiments. It is generally placed in contact with or immediately next to the breast, and hand expression is used to express colostrum into the interface 142. The plunger of the attached syringe 104, 105 is then pulled back to draw the colostrum into the syringe. Thus, unlike the previously described embodiment, the interface 142 is not used to apply suction force to the breast.

Figure 12A:
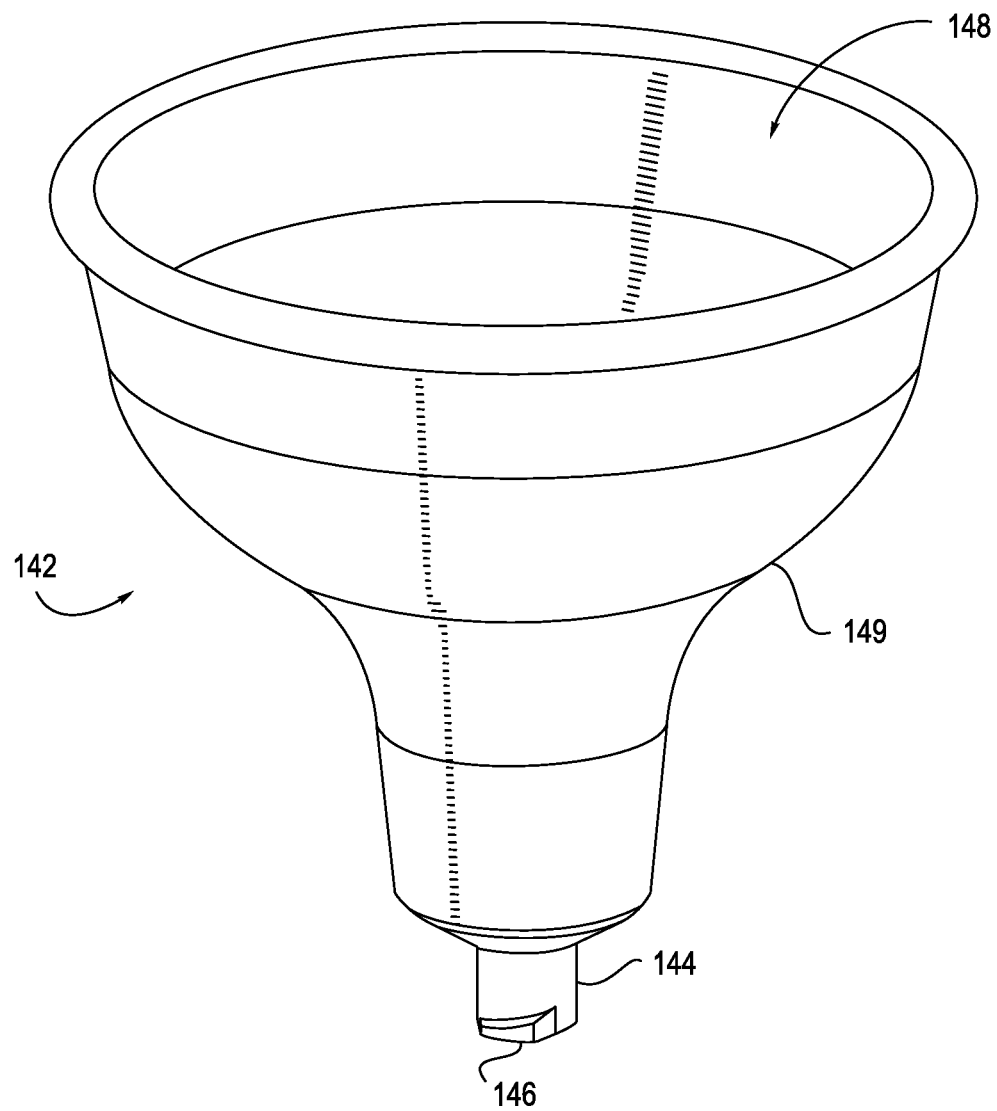
FIGS. 12A and 12B are perspective and side views, respectively, of an interface of FIG. 11.
Figure 12B:
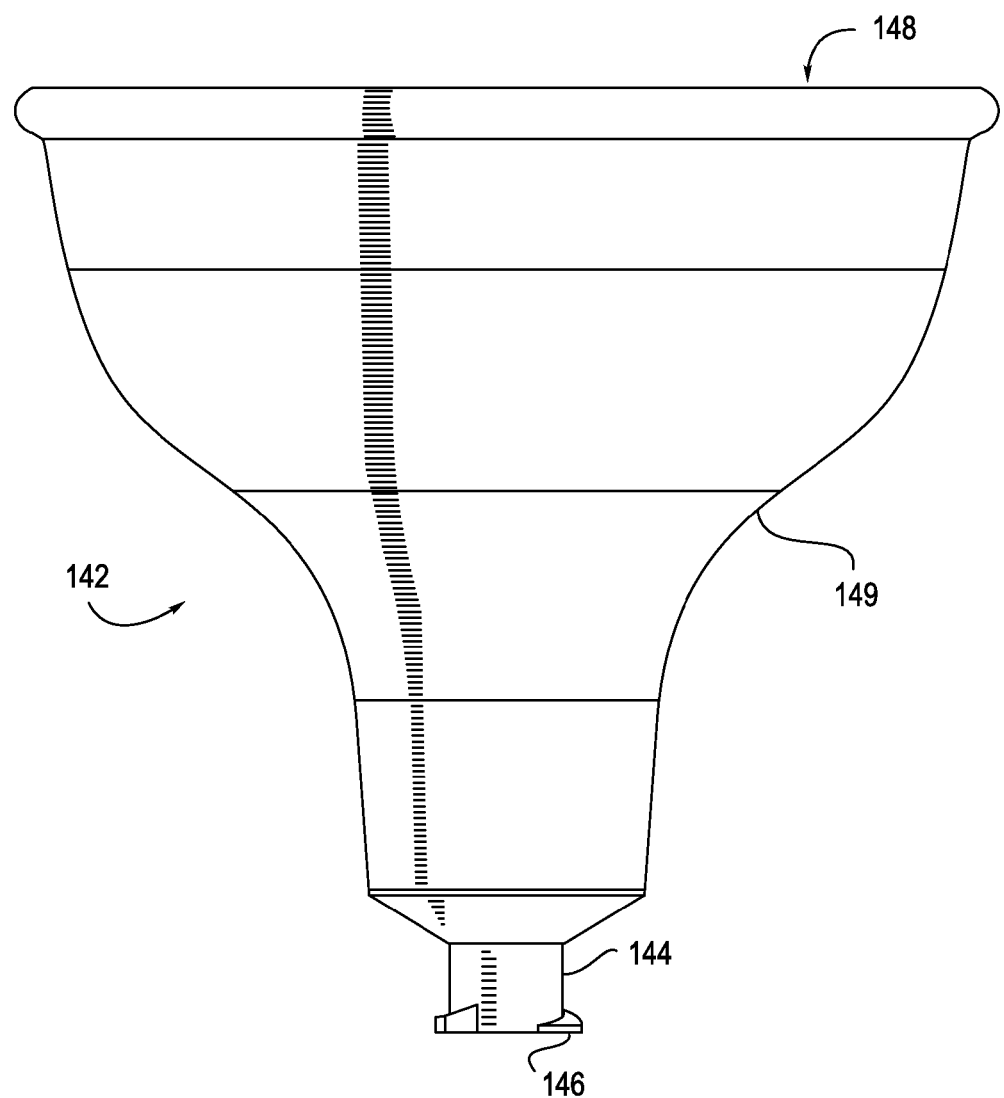

FIGS. 12A and 12B show the interface 142 in greater detail. In this embodiment, the curved surface 149 acts as an ergonomic feature to make the interface 142 easier to hold. Alternative embodiments may have other suitable shapes and/or features, such as but not limited to bumps, ridges or the like, to further facilitate handling the interface 142.

Figure 13:
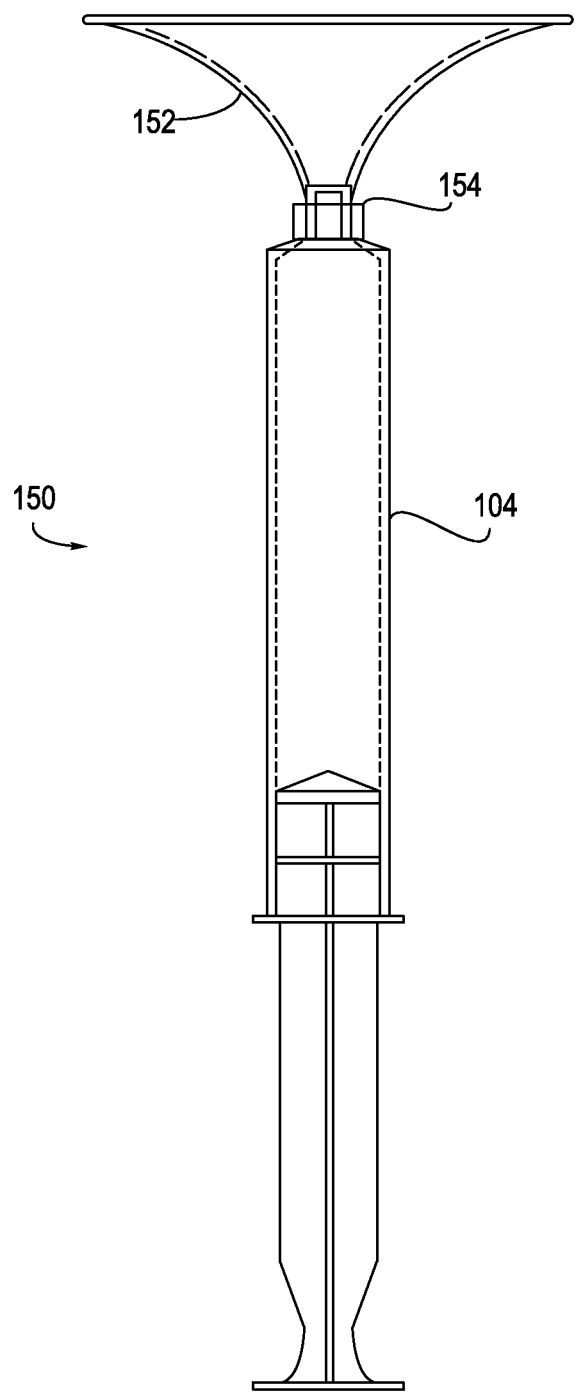
FIG. 13 is a side view of a system for collecting and administering colostrum/milk, in accordance with another alternative embodiment.

Referring now to FIG. 13, in another embodiment, a system 150 for colostrum collection and dispensation may include another embodiment of an interface 142, coupled with the syringe/suction member 104 via a Luer connection 154. (Of note, any of the above-described interface embodiments may also connect to syringes via Luer connections.) This embodiment is similar to that described in reference to FIG. 12, although the interface 152 has a funnel shape. This interface 152 may be made of any suitable material, and in various embodiments it can either be used to apply suction to the breast by contacting breast tissue surrounding the nipple and applying suction force, or it may simply be used to collect colostrum and allow it to pass into the syringe 104.

Figure 14A:
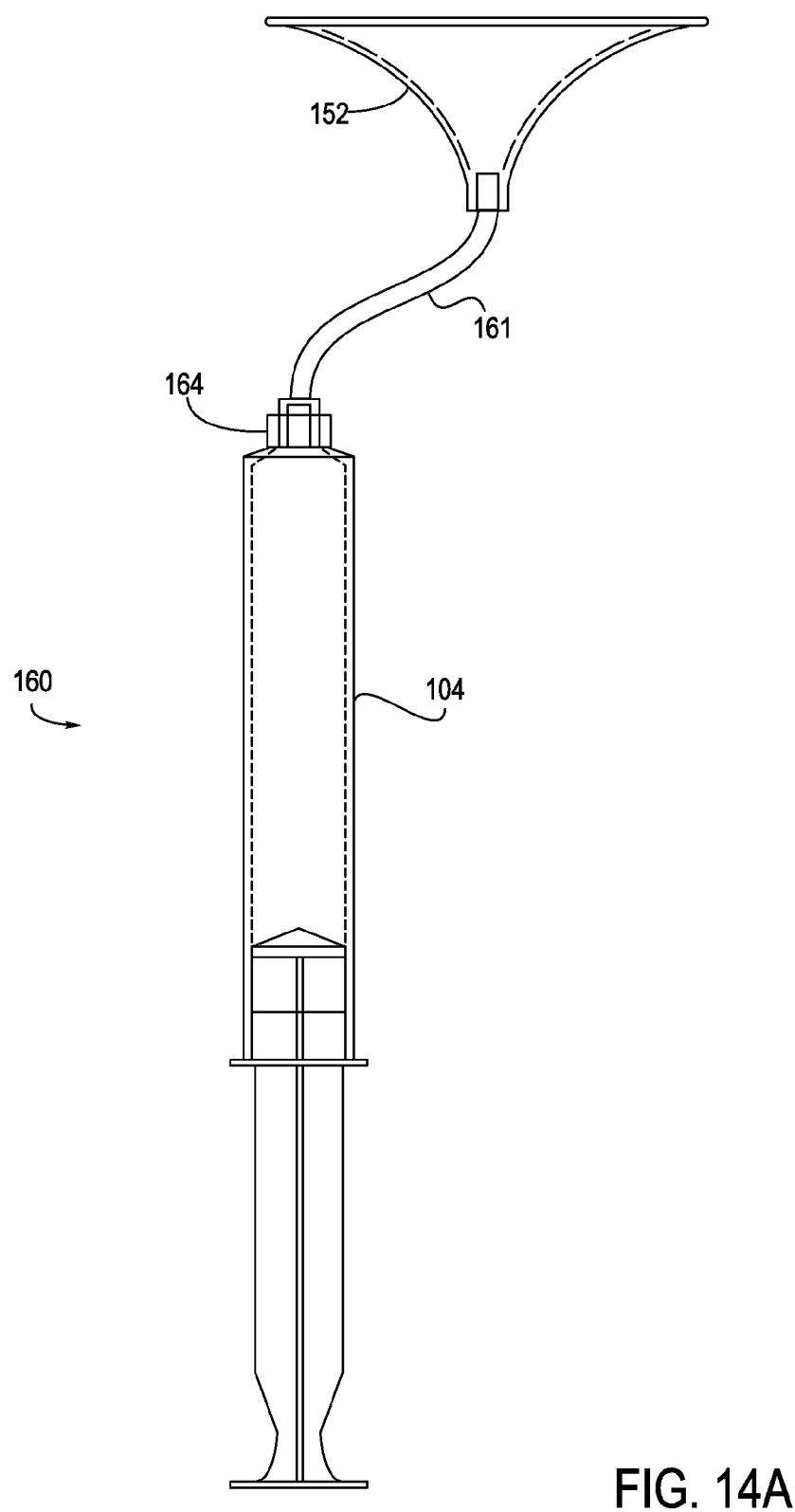
FIGS. 14A-14C are side views of a system for collecting and administering colostrum/milk, including various optional components, in accordance with various alternative embodiments.
Figure 14B:
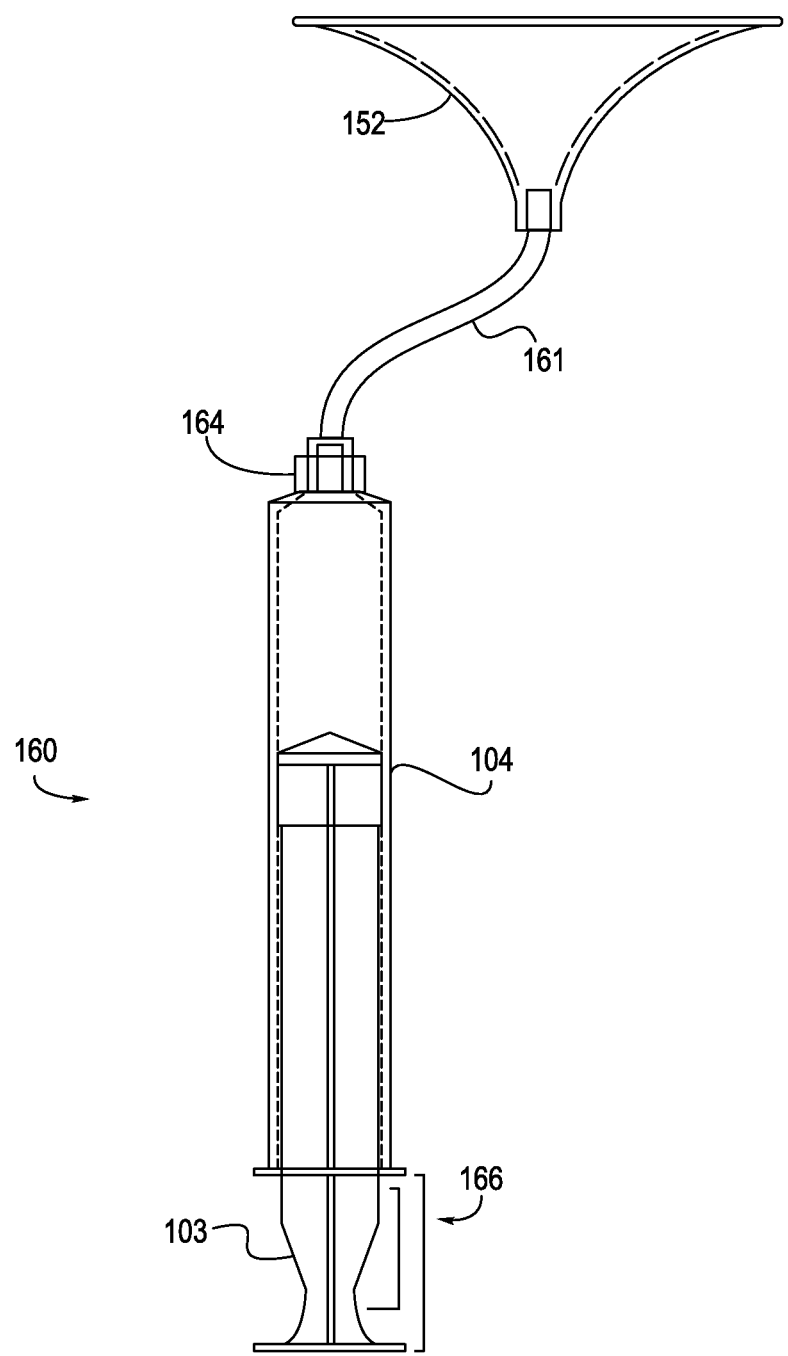

FIG. 14A shows another alternative embodiment of a colostrum collection and administration system 160, in which a flexible conduit connects at one end to the interface 152 and at an opposite end to the syringe 104 via a Luer connection 164.

FIG. 14A shows another alternative embodiment of a colostrum collection and administration system 160, in which a flexible conduit 161 connects at one end to the interface 152 and at an opposite end to the syringe 104 via a Luer connection 164.

Figure 14C:
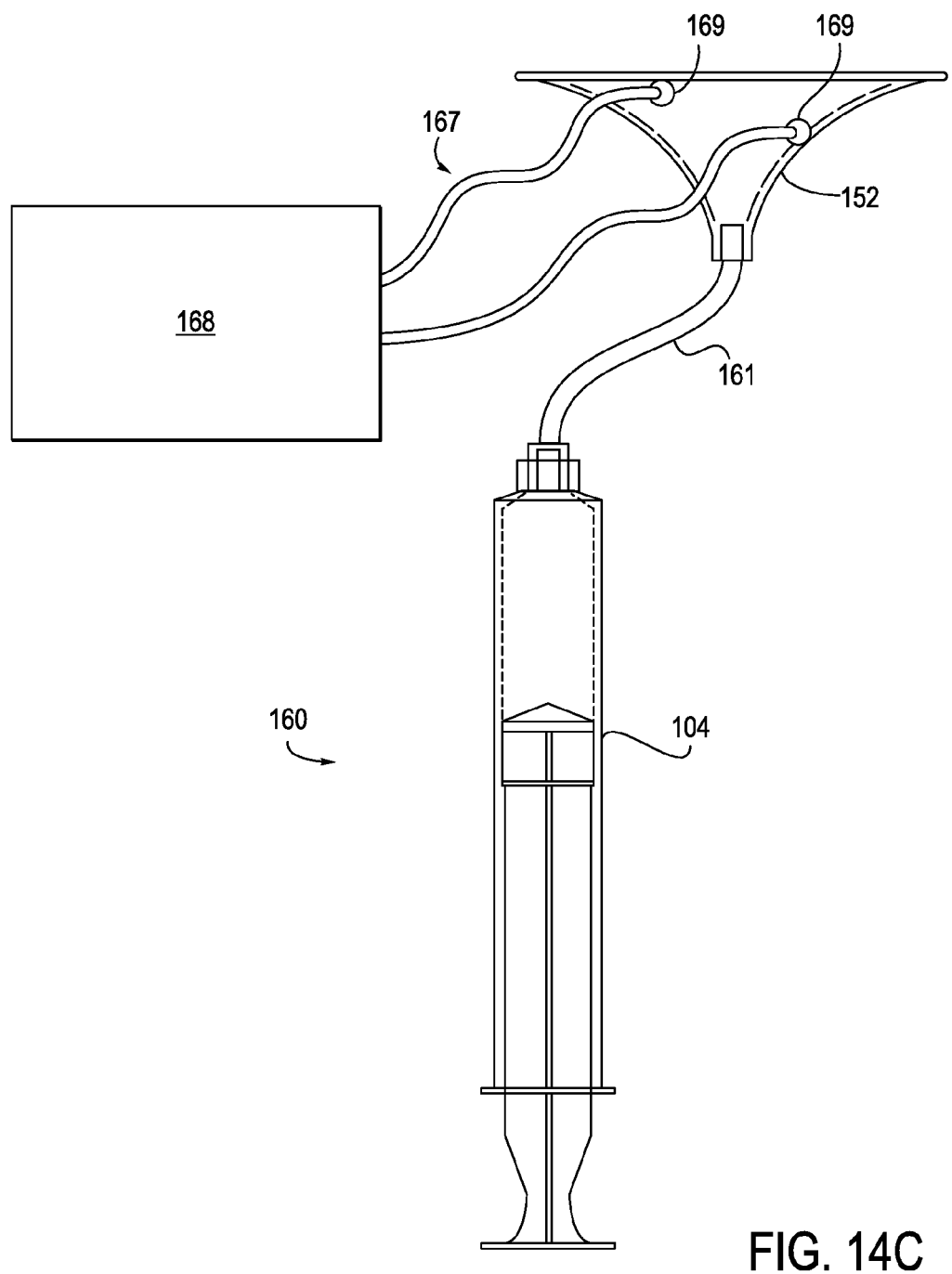

FIG. 14C shows the system 160 of FIG. 14A with an optional power source/controller 168 connected via wires 167 to electrodes 169, which are connected to the interface 152. The electrodes 169 are situated on the interface 152 such that direct contact is made with breast tissue when in use. The power source/controller 168 is used to deliver energy to the electrodes 169, to help stimulate colostrum secretion.

Figure 15A:
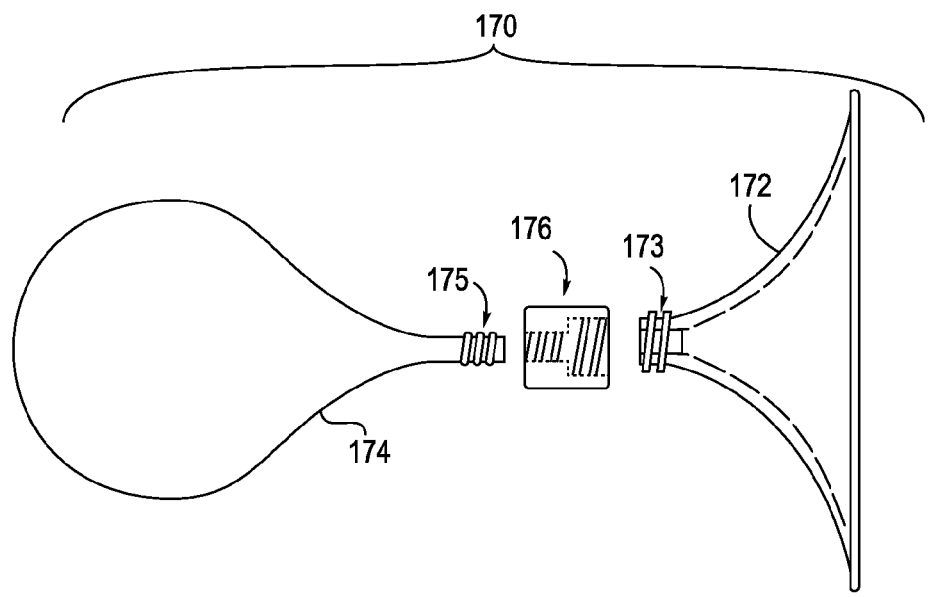
FIGS. 15A-15D are side views of a system for collecting and administering colostrum/milk, including various optional components, in accordance with various alternative embodiments.
Figure 15B:
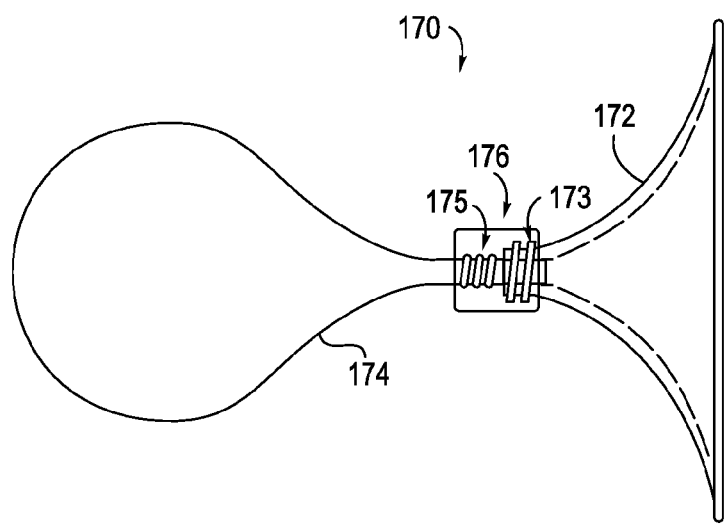

Referring now to FIGS. 15A and 15B, in another alternative embodiment, a colostrum collection and dispensing system 170 may include an interface having a connecting end 173, a bulb suction member 174 having a connecting end 175, and a connector 176 having internal helical threads that mate with threads on the two connecting ends 173, 175. In some embodiments, the connector 176 may form a seal with one or both of the connecting ends 173, 175 when fully connected. In this embodiment, the bulb suction member 174 generates suction force to draw colostrum into its internal space from the interface 172.

Figure 15C:
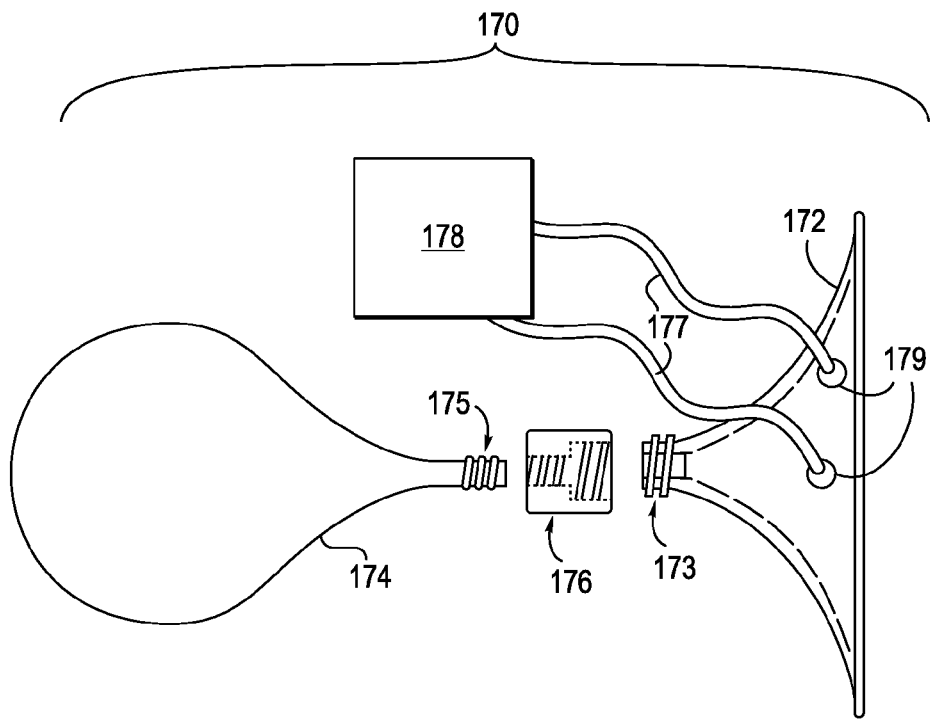
Figure 15D:
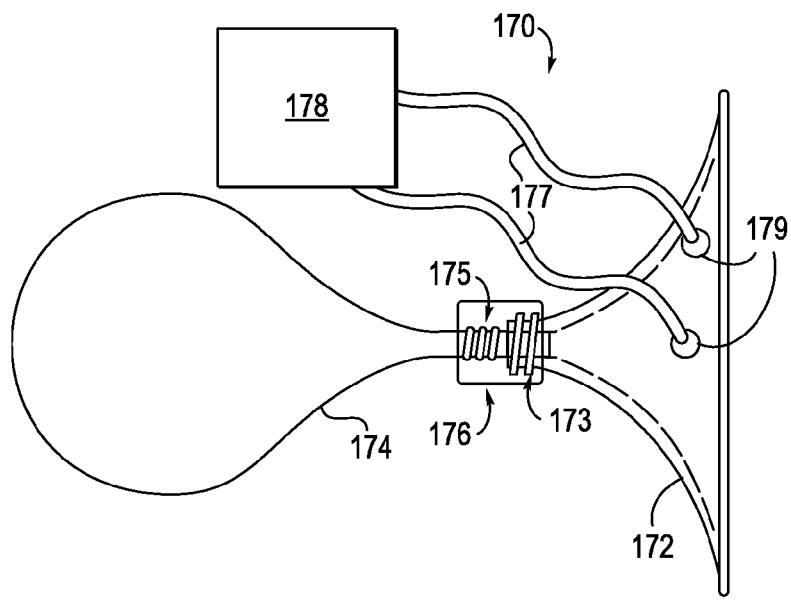

FIGS. 15C and 15D show the system 170 of FIGS. 15A and 15B with an optional power source/controller 178 connected via wires 177 to electrodes 179, which are connected to the interface 172. The electrodes 179 are situated on the interface 172 such that direct contact is made with breast tissue when in use. The power source/controller 178 is used to deliver energy to the electrodes 179, to help stimulate colostrum secretion.

Figure 16:
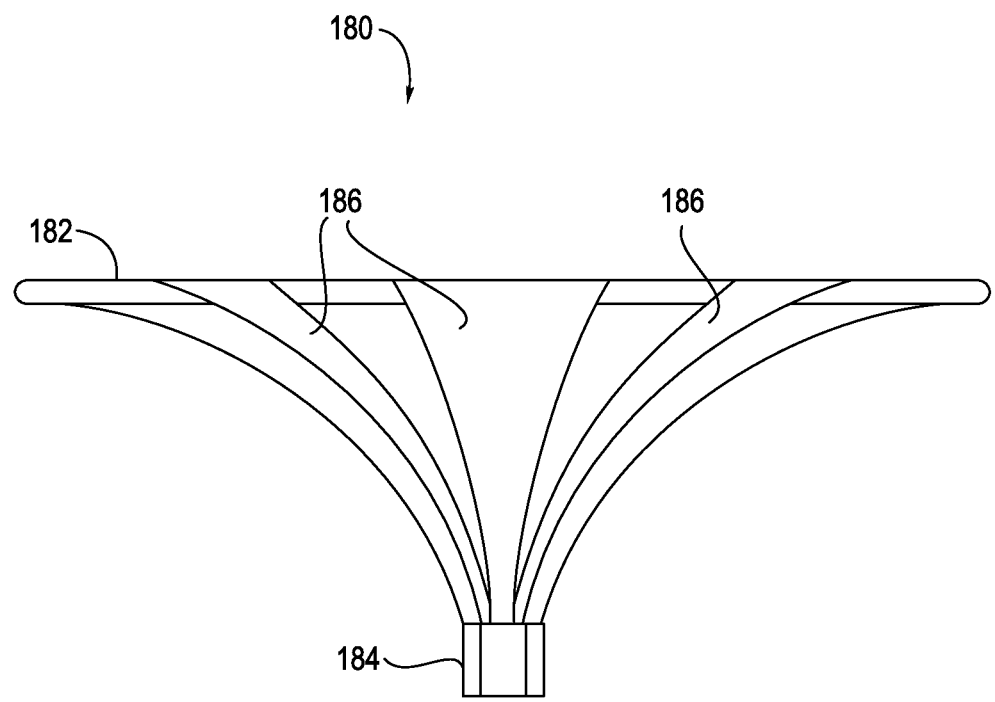
FIG. 16 is a side view of an interface of a system for collecting and administering colostrum/milk, in accordance with one embodiment.

Referring now to FIG. 16, in one embodiment, an interface 180 (shown here in cross-section) may include a flared end 182 for collecting colostrum, a tapered shape that tapers down to a connector end 184 for connecting to a syringe or other suction member, and multiple, vertically oriented ridges 186, in an alternating narrow/wide configuration, which serve as flow channels to help enhance flow of colostrum into the syringe or other suction member. In other embodiments, the ridges 186 may be replaced by indentations, grooves or any other suitable surface feature. These ridges 186 or other features are optional, however, and some embodiments of interfaces may not include any internal surface features.

Figure 17A:
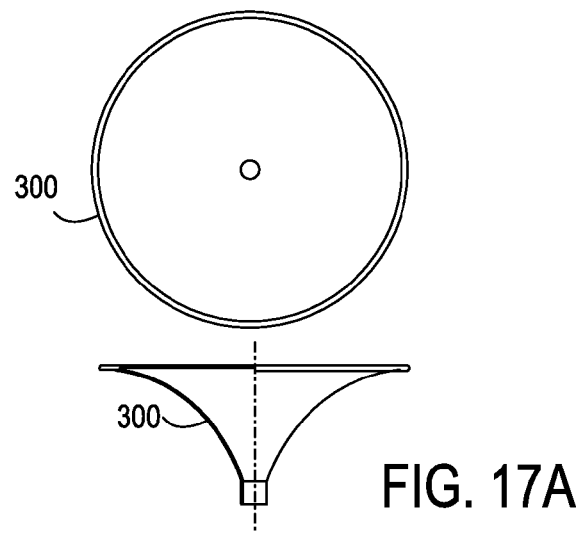
FIGS. 17A-17C are various views of several interfaces of systems for collecting and administering colostrum/milk, in accordance with various alternative embodiments.
Figure 17B:
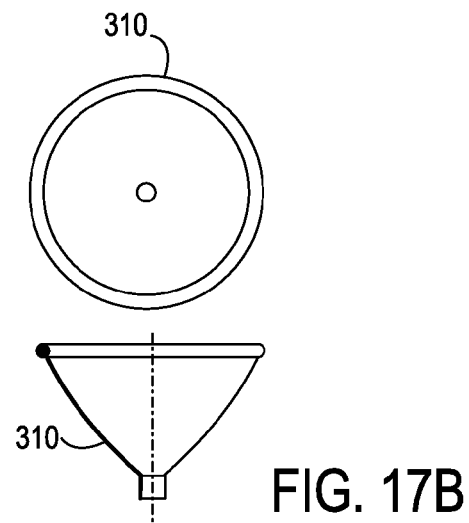
Figure 17C:
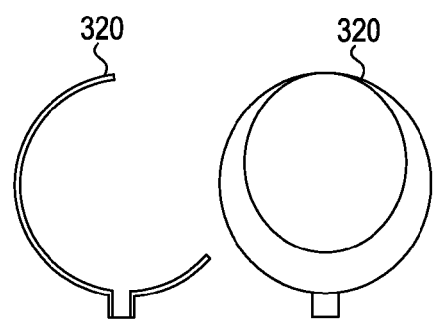

FIGS. 17A-17C illustrate three embodiments of interfaces. FIG. 17A illustrates a concave interface 300 (side view at bottom, top view at top). FIG. 17B illustrates a convex interface 310 (side view at bottom, top view at top). FIG. 17C illustrates a spherical interface 320 (side view at left, front view at right). As these embodiments illustrate, interfaces may have any of a number of suitable sizes, shapes and configurations, according to various alternative embodiments.

Figure 18A:
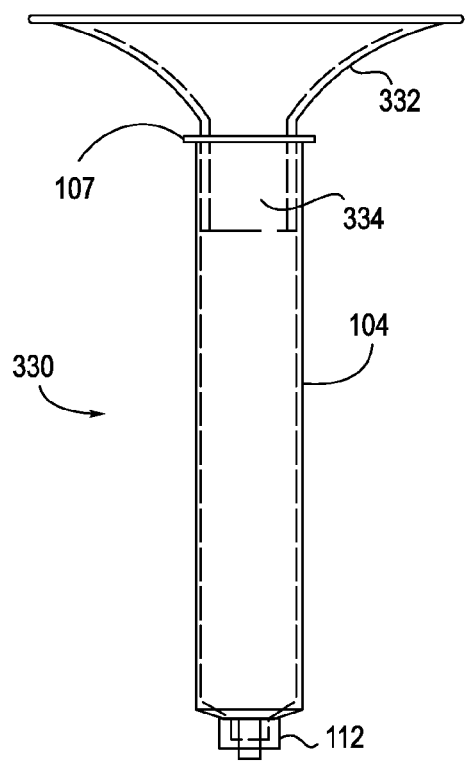
FIGS. 18A and 18B are side and perspective views, respectively, of a system for collecting and administering colostrum/milk, in accordance with another alternative embodiment.
Figure 18B:
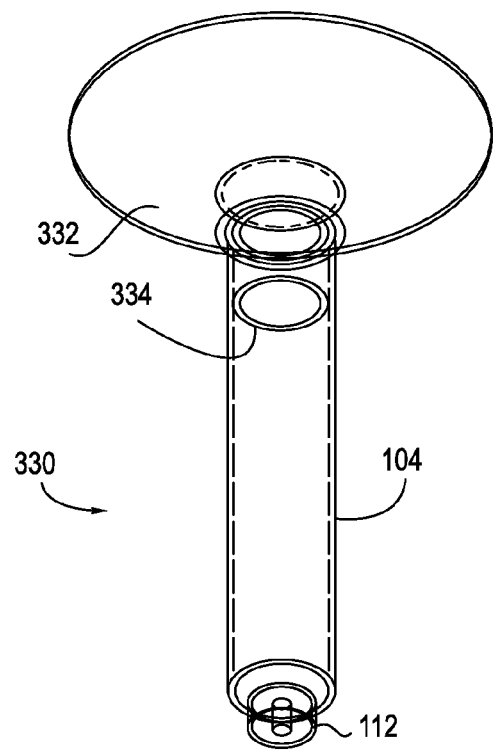

Referring now to FIGS. 18A and 18B, in yet another embodiment, a system 330 for colostrum collection and administration may include an interface 332 with a relative wide connection end 334, which fits into an open end 107 of a syringe 104. In this embodiment, the Luer end 112 of the syringe 104 is thus left free to connect with another device. In various embodiments, the interface 332 may be either permanently or reversibly attached to the open end of the syringe 104.

Figure 19:
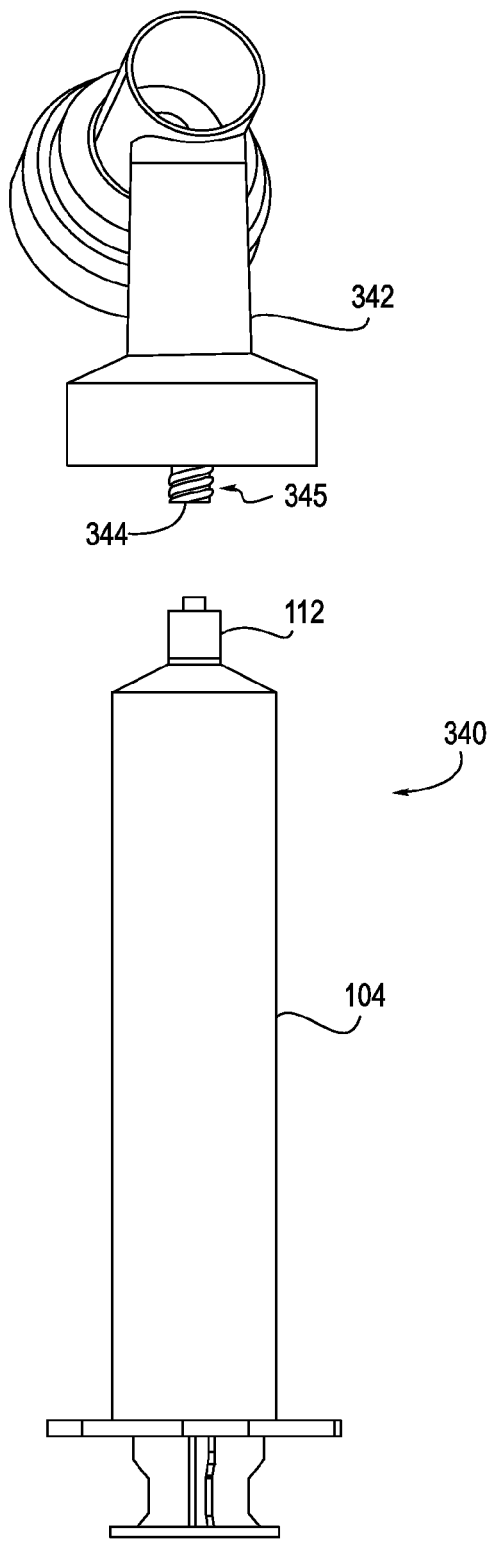
FIG. 19 is a side view of a system for collecting and administering colostrum/milk, in accordance with another alternative embodiment.

With reference now to FIG. 19, in another alternative embodiment, a colostrum collection and administration system 340 may include an interface 342 that has a connector portion 344 with threads 345 configured to engage with inner surface threads on a syringe 104 with a Luer connector 112. In this embodiment, the interface 342 is a breast shield for use with any standard or yet-to-be-designed breast pump system. This embodiment does not require an adapter between the interface 342 and the syringe 104.

Figure 20A:
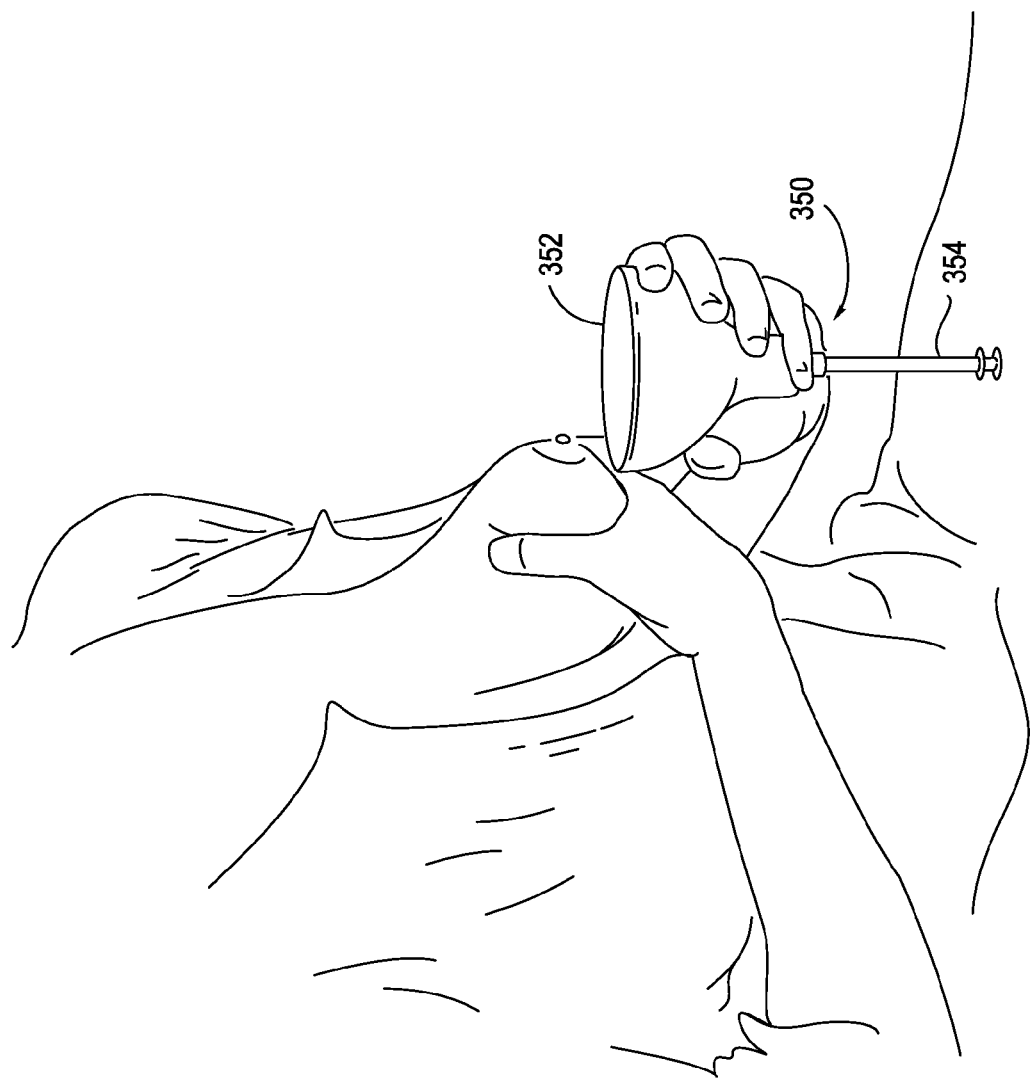
FIGS. 20A-20D illustrate a method for a system for collecting and administering colostrum, in accordance with various alternative embodiments.

Referring now to FIGS. 20A-20D, two embodiments of a method for collecting and dispensing colostrum are described. In FIG. 20A, a system 350, including an interface 352 and an attached syringe/suction member 354 is positioned near the breast and below the nipple of the breast. Colostrum is expressed into the interface 352 using hand expression. The colostrum may then be drawn into the syringe 354 by pulling back the plunger of the syringe 354.

Figure 20B:
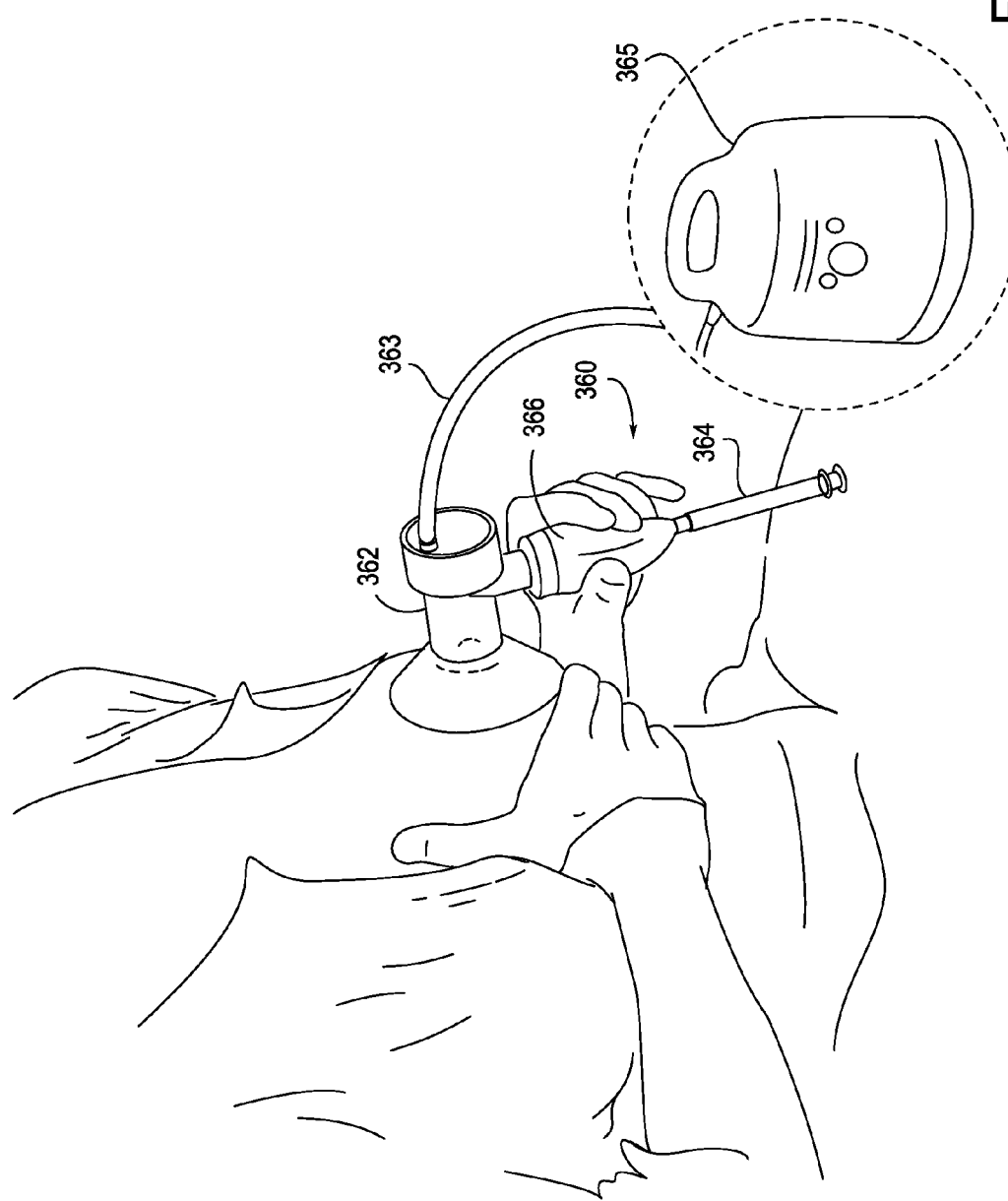

FIG. 20B illustrates another embodiment, in which a system 360 includes an interface 362, a syringe/suction member 364, and an adapter 366 connecting the two. The interface 362, in this embodiment, is a breast shield coupled to a breast pump 365 via a tube 363. Using this embodiment, colostrum expression may be stimulated by the breast pump 365 and interface 362, with or without additional hand expression. Again, colostrum may then be drawn into the syringe 364 by pulling back the plunger of the syringe 364.

Figure 20C:
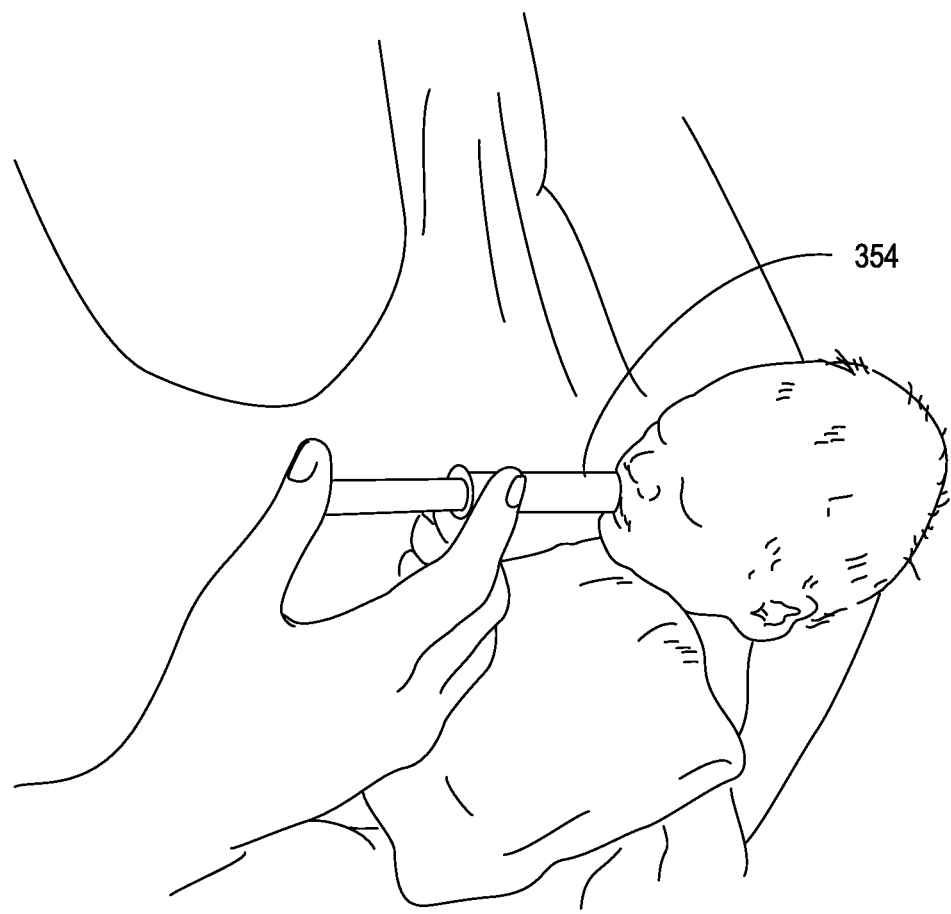

Referring now to FIG. 20C, whichever of the methods and systems is used to collect the colostrum, in one embodiment, the colostrum is then fed to the newborn by simply detaching the syringe 354 from the system and using the syringe to feed the newborn by mouth. As mentioned previously, this method eliminates the step used in current methods of drawing the colostrum into a syringe from an open container.

Figure 20D:
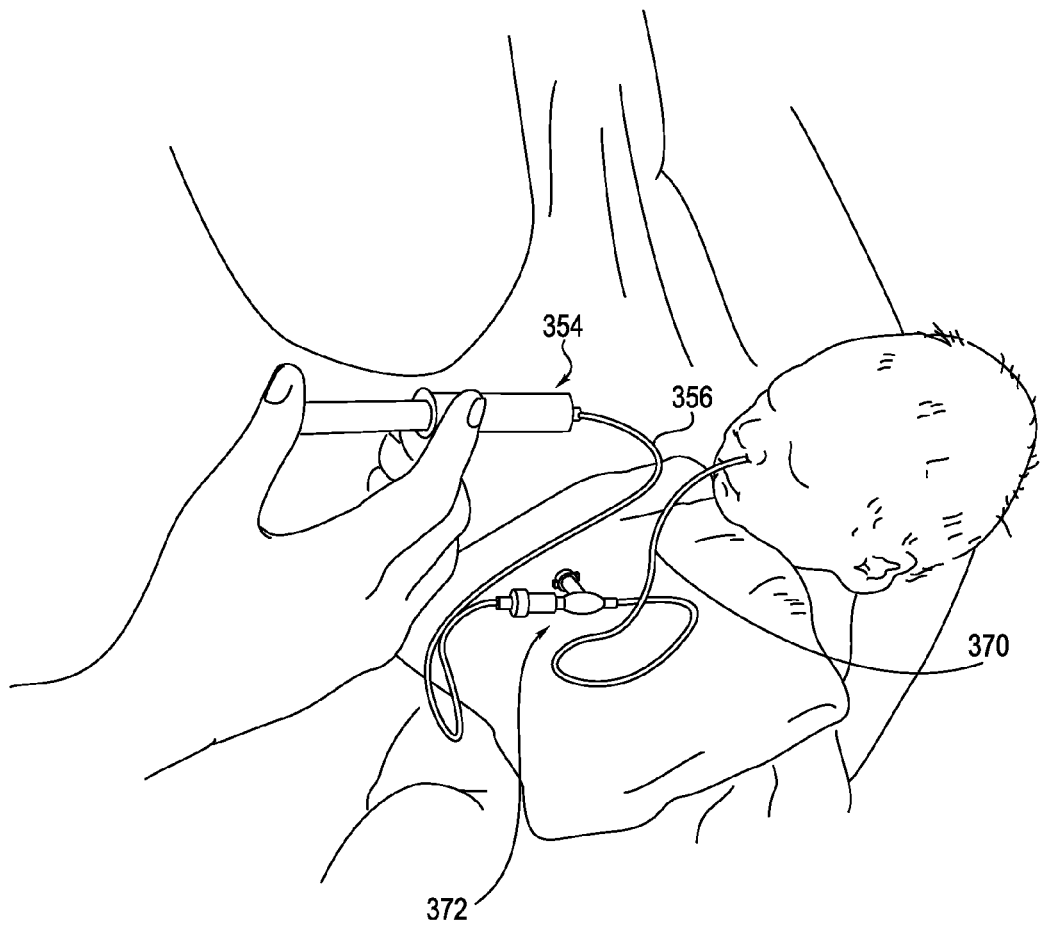

In an alternative embodiment pictured in FIG. 20D, the syringe 354 may be attached to a flexible tube 356 for feeding the newborn. In some embodiments, as shown, the flexible tube 356 may be attached, via a connector 372, to a previously inserted feeding tube 370. In alternative embodiments (not shown), the flexible tube 356 itself may be advanced into the mouth or a nostril of the newborn and used to directly advance the colostrum into the throat.

A number of variations, including additional steps, different steps, different system components and the like may be made to the method embodiments described in relation to FIGS. 20A-20D. Any such variations should be interpreted as being within the scope of the claims.

Figure 21:
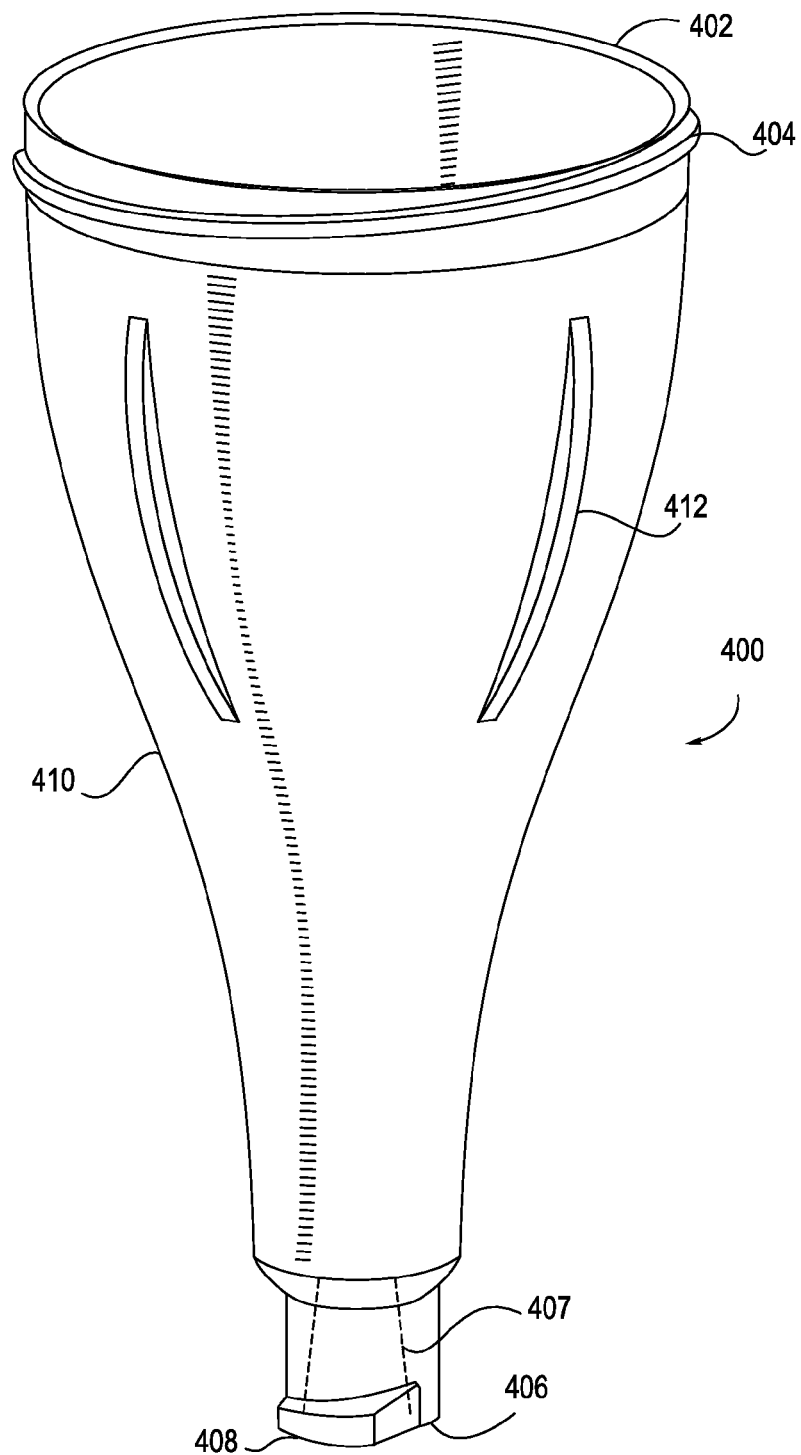
FIG. 21 is a perspective view of a combination manual expression colostrum collector and breast pump adapter, in accordance with one embodiment.

Referring now to FIG. 21, in another alternative embodiment, a combination colostrum collection device/breast shield adapter 400 may be provided. In this embodiment, the combination device 400 may be used both for facilitating collection of colostrum by manual expression and also for attaching to any breast pump shield for colostrum expression using a breast pump system. In the embodiment shown, the combination device 400 includes a large-diameter, colostrum collection end 402, including one or more breast shield threads 404, a small-diameter, syringe-coupling end 406, including one or more syringe threads 408 and a tapered inner surface 407 for mating via press fit with a distal end of a syringe, a contoured, tapered surface 410 between the two ends 402, 406, and optional grip members 412 for facilitating holding the device 400 with a hand and preventing slipping.

In various embodiments, the breast pump shield thread(s) 404 may be compatible with any known or yet-to-be-invented breast pump shield. In some embodiments, the thread(s) 404 of one combination device 400 may be compatible with one or more complementary threads of multiple different breast shields. Alternatively, each device 400 may be compatible with one or more breast shields but not all breast shields, and multiple different devices 400, each having different breast shield threads 404, may be available for compatibility with different breast pump systems. Similarly, in various embodiments, the syringe thread(s) 408 may be compatible with any known or yet-to-be-invented syringe. Alternatively, if a colostrum collection device other than a syringe is used, the syringe thread(s) 408 may be designed to be compatible with such device(s). In some embodiments, the syringe thread(s) 408 of one combination collection/adapter device 400 may be compatible with one or more complementary threads of multiple different syringes. Alternatively, each device 400 may be compatible with one or more syringes but not all syringes, and multiple different devices 400, each having different syringe threads 408, may be available for compatibility with different breast pump systems.

In the embodiment shown in FIG. 21, the small-diameter end 406 includes both the syringe thread(s) 408 and a tapered inner surface 407. These two features allow the small-diameter end 406 to be compatible with many different types of syringes. Specifically, the external-surface syringe thread(s) 408 allow the small-diameter end 406 to connect with Luer syringes, as are commonly used in a hospital setting. The tapered inner surface 407 is designed to admit and mate with a tapered distal end of an enteral syringe via press fit (or "pressure fit"). Enteral syringes are typically small volume syringes used in hospitals or outside hospitals for feeding newborns. In alternative embodiments, the combination device 400 may include only the external thread(s) 408 or only the tapered inner surface 407, but including both in one embodiment will facilitate compatibility with multiple types of syringes.

In various embodiments, the combination device 400 may have any suitable size, shape, contour and overall design, as long as the collection end 402 is compatible with a breast pump shield and the syringe end 406 is compatible with a syringe or other colostrum collection device. In the embodiment shown, the surface of the device 400 contours/tapers gradually from the collection end 402 to the syringe end 406, and this shape may provide ergonomic advantages, in that it is likely easy for a user to hold in one hand. The optional grip members 412 may also facilitate holding the device 400 in one hand and may help prevent the device 400 from slipping out of the hand. In various alternative embodiments, the grip members 412 may be replaced with other types/shapes of grip members, a textured surface and/or the like. As with all the embodiments described thus far, the device 400 may be made of any suitable material, such as but not limited to plastic. The device 400 is typically disposable but may alternatively be made of a material that can be sterilized after use and reused.

Figure 22C:
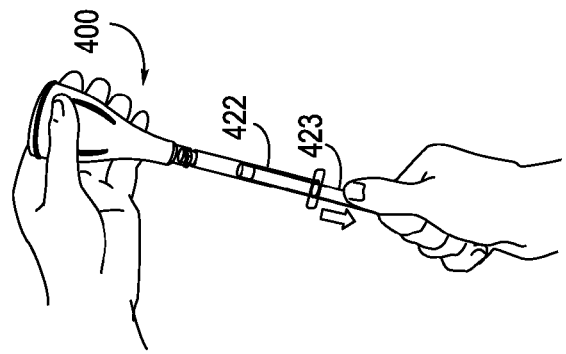
FIGS. 22A-22G illustrate a method of using a system for collecting and administering colostrum, including the combination device of FIG. 21, a syringe and a breast pump device, in accordance with one embodiment.
Figure 22B:
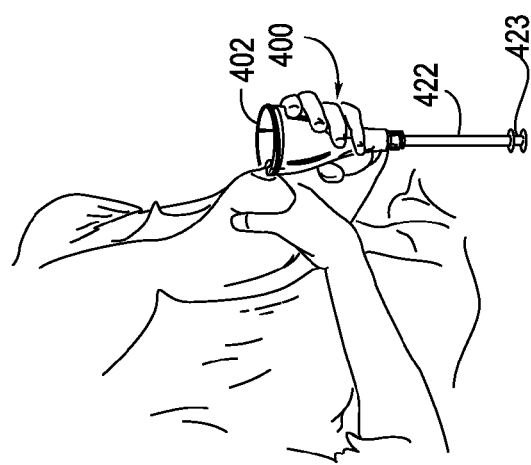
Figure 22A:
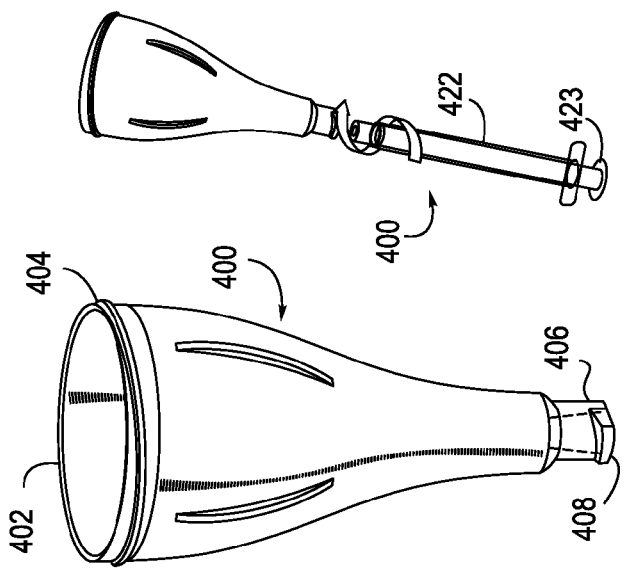

Referring now to FIGS. 22A-22G, one embodiment of a method will be described for using a colostrum collection/administration system 420, where the system includes the combination collection/adapter device 400 as described in FIG. 21. Referring first to FIG. 22A, a first step in the method may include connecting the combination device 400 with a syringe 422, by twisting the distal end of the syringe into the complementary tapered inner surface 407 of the combination device 400. (The syringe 422 includes a plunger 423.)

Referring to FIG. 22B, in one embodiment of the method, a next step may involve hand expressing colostrum from a breast into the open, collection end 402 of the combination device 400, which is connected at its opposite end to the syringe 422. Hand expression may be performed for any suitable length of time, such as such as but not limited to a few minutes to as many as fifteen minutes or more, or in one specific embodiment for about ten minutes. In one embodiment, colostrum may be hand expressed from one breast during this step. Alternatively, colostrum may be hand expressed from both breasts during this step.

Referring now to FIG. 22C, after hand expressing from one or both breasts, an optional step of retracting the plunger 423 of the syringe may be performed. Retracting the plunger 423 produces a suction force and pulls the colostrum from the combination device 400 into the syringe 422. This step is optional at this stage of the method, because alternatively the plunger 423 can simply be retracted later, after further colostrum extraction using a breast pump.

Figure 22E:
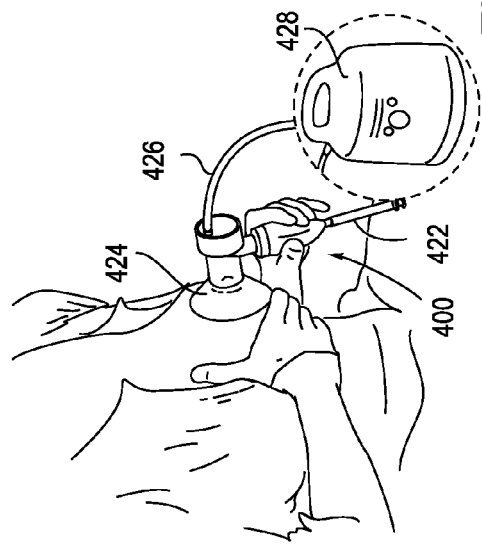
Figure 22G:
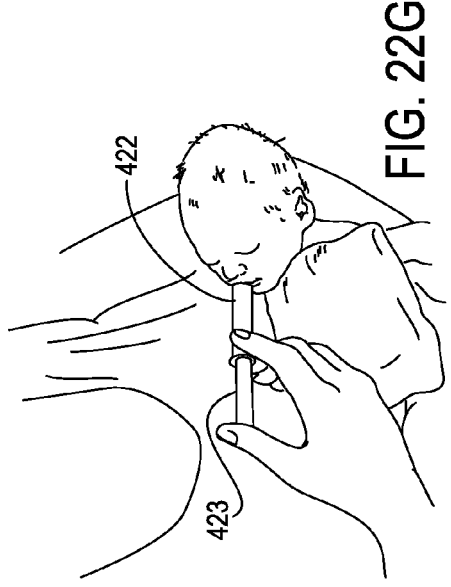
Figure 22D:
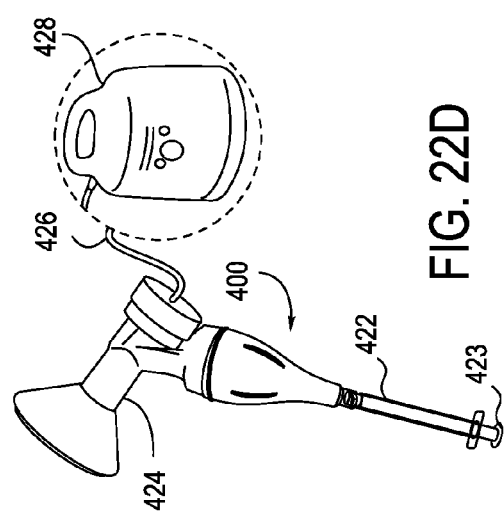

Referring now to FIG. 22D, in a next step, the combination device 400 may be connected to a breast pump shield 424. The breast pump shield 424 may be part of a breast pump system, including a connection tube 426 and a source of suction 428. The breast shield 424 may be connected to the collection end 402 of the device 400 via one or more breast shield threads 404 and complementary thread(s) on the breast pump shield.

Referring to FIG. 22E, the breast shield 424 and the other components of the breast pump system (tube 426 and suction source 428) may then be used to extract additional colostrum from the breast. Similar to hand expression, breast pumping may be performed for any suitable time, such as but not limited to a few minutes to as many as fifteen minutes or more, or in one specific embodiment for about ten minutes. In one alternative embodiment, breast pumping may be performed before hand expression. In other alternative embodiments, breast pumping alone or hand expression alone may be performed.

Figure 22F:
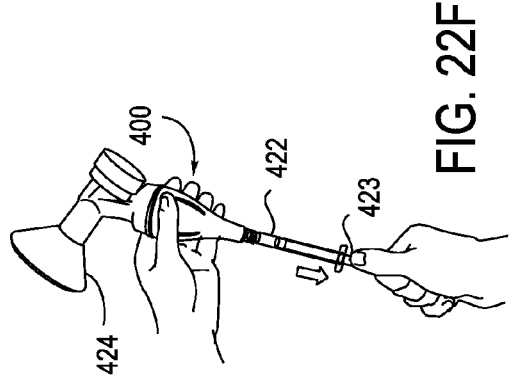

Referring now to FIG. 22F, after colostrum has been breast pump expressed from one or both breasts, the plunger 423 of the syringe 422 may be pulled back to generate a suction force and thus pull colostrum from the combination device 400 into the syringe 422. As described above, this step may be performed one or more times during the method, for example partially retracting the plunger 423 each time as colostrum is expressed, or it may be performed after all the colostrum expression steps are completed.

Finally, referring now to FIG. 22G, once the colostrum is pulled into the syringe 422 by retracting the plunger 423, the combination device 400 may be removed from the syringe 422, with the syringe 422 now containing the colostrum. Once the syringe 422 is removed from the combination device 400, the syringe 422 can then be used to administer the colostrum to the newborn by inserting the distal end of the syringe 422 into the newborn's mouth and depressing the plunger 423. In an alternative embodiment, a tube may be connected to the distal end of the syringe 422 and advanced into a newborn's nose or mouth for feeding. In other alternative embodiments, other colostrum containment/delivery devices may be connectable with the combination device 400 and used both for collecting and holding the colostrum as well as for administering the colostrum to the newborn. Such alternative containment/delivery devices may include vials, jars, bottles, tubes or the like.

Referring now to FIGS. 23A-23G, an alternative embodiment of a colostrum collection device 500 is illustrated. The views in the various figures are perspective (FIG. 23A), top down (FIG. 23B), side (FIGS. 23C and 23D), cross-sectional through lines A-A of FIG. 23D (FIG. 23E), bottom up (FIG. 23F) and cross-sectional through lines B-B of FIG. 23F (FIG. 23G). In some cases, the collection device 500 may also be used as a breast shield for use with a breast pump. In the embodiment shown, the collection device 500 includes a large-diameter, colostrum collection end 502, a small-diameter, syringe-coupling end 506, including one or more syringe threads 508 (or "luer lock threads") for mating with a distal end of a syringe, a tapered outer surface 510 and corresponding inner surface 514 between the two ends 502, 506, and optional grip members 512 (or "ribs") for facilitating holding the collection device 500 with a hand, preventing slipping and adding structural support to the device 500.

FIGS. 23A-23G illustrate various views and details of the collection device 500. Any of the features, materials, and configurations described for alternative embodiments above may be applied to the collection device 500. One of the differences between the collection device 500 and previously described embodiments is the lack of threads on the collection end 502. Another difference is the approximately straight inner surface 514, as compared to some previously described embodiments that have a curved surface. The straight inner surface 514 may be advantageous in that colostrum collected at the collection end 502 may tend to slide more easily down the straight inner surface 514 than down a curved one. In the embodiment shown, the straight inner surface 514 and corresponding outer surface 510 are approximately straight along a majority of their length but curve slightly outward as they approach the collection end 502 and bend slightly toward the syringe-coupling end 506 of the device 500. In an alternative embodiment, the outward curve at the collection end 502 may be eliminated. The cylindrical portion at the syringe-coupling end 506, or in alternative embodiments a slightly different shape, will typically be retained, for facilitating coupling with a syringe.

In various embodiments, the syringe threads 508 may be compatible with any known or yet-to-be-invented syringe. Alternatively, if a colostrum collection device other than a syringe is used, the syringe threads 508 may be designed to be compatible with such device. In some embodiments, the syringe threads 508 may be compatible with one or more complementary threads of multiple different syringes. Alternatively, each device 500 may be compatible with one or more syringes but not all syringes, and multiple different devices 500, each having different syringe threads 508, may be available.

Figure 24A:
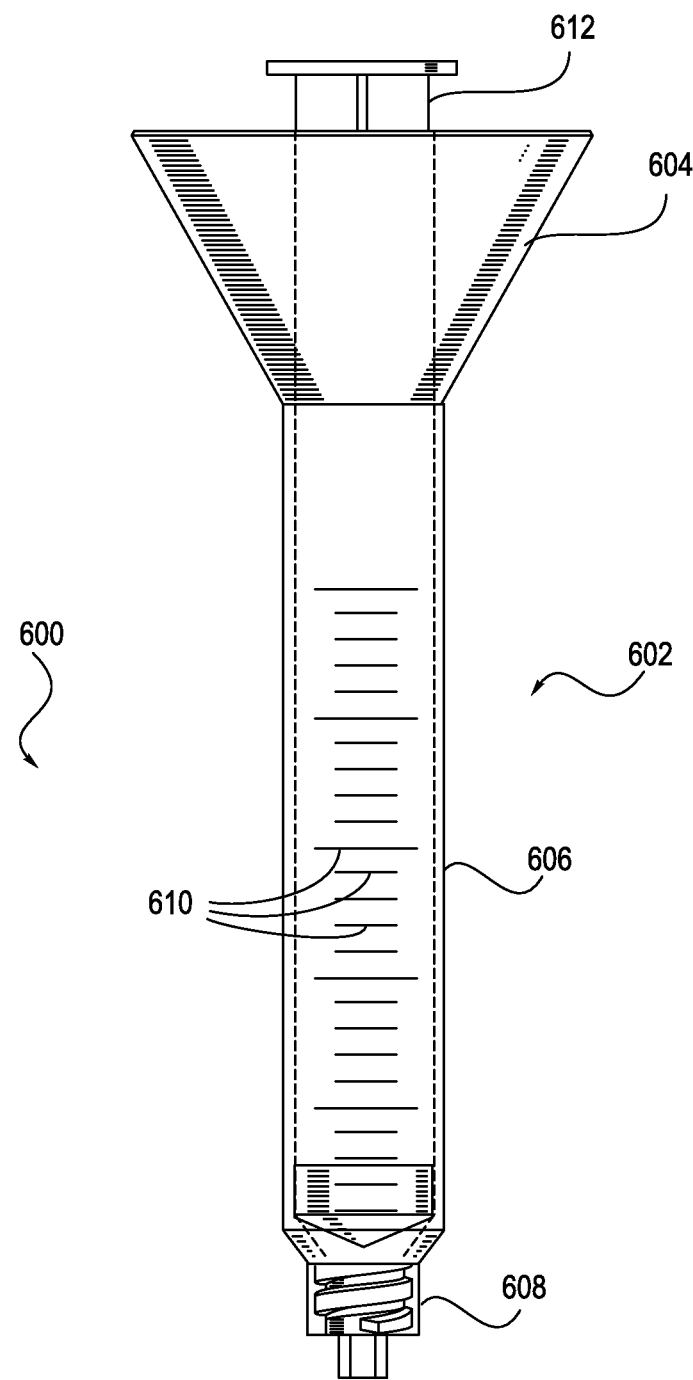
FIGS. 24A and 24B are side and exploded views, respectively, of a colostrum collection and delivery device configured to resemble a syringe with a funnel end, according to one embodiment.
Figure 24B:
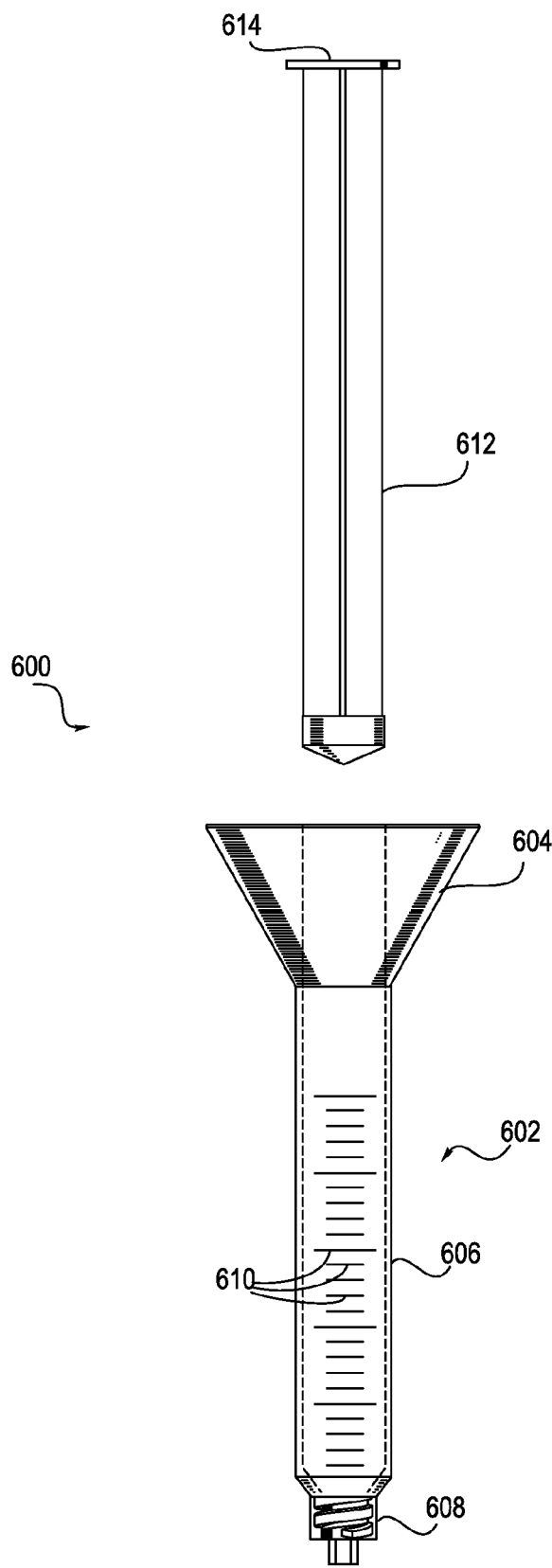

Referring now to FIGS. 24A and 24B, another embodiment of a colostrum collection device 600 may be configured similar to a syringe but with a wide, funnel-shaped proximal end for facilitating colostrum collection. In the embodiment shown, the collection device 600 includes a colostrum collection member 602 and a plunger 612. The colostrum collection member includes a proximal funnel portion 604, a middle cylindrical portion 606, a distal narrow portion 608, and a number of optional fluid level markers 610. The plunger 612 includes a proximal flat portion 614 and a distal stopper portion 616, which is typically but not necessarily made of rubber. In all respects, the colostrum collection device 600 may function like a syringe, but it also includes the additional feature of the funnel portion 604, which will likely facilitate collection of colostrum expressed from a breast. Colostrum collected in the colostrum collection member 602 may be simply advanced out of the end of the distal narrow portion 608 by advancing the plunger 612 into and through the collection member 602. The distal narrow portion 608 may be positioned in a newborn's mouth, or alternatively a tube may be attached to the distal narrow portion 608 and used to feed the newborn.

Although particular embodiments have been shown and described, they are not intended to limit the claims included with this application. Various changes and modifications may be made to any of the embodiments, without departing from the spirit and scope of the claims. The claims are intended to cover alternatives, modifications, and equivalents. For example, any of the devices, systems and methods described above may be used with any suitable syringes and/or with any suitable breast pump systems. None of the above descriptions should be interpreted as limiting any of the embodiments to use with any particular syringe and/or breast pump systems.

What is claimed is:

1. A method of collecting colostrum from a breast of a human and dispensing the colostrum to a newborn, the method comprising:
   providing a colostrum collection device, comprising:
      a large-diameter colostrum collection end comprising a breast shield thread for connecting the colostrum collection device with a breast shield of a breast pump system; and
      a small-diameter syringe-coupling end, comprising a syringe thread for connecting the small-diameter syringe-coupling end with a threaded distal end of a syringe;
   coupling the small-diameter syringe-coupling end of the colostrum collection device with the syringe;
   manually expressing colostrum from the breast into the large-diameter colostrum collection end of the colostrum collection device;
   retracting a plunger of the syringe to create a suction force and thus cause the colostrum to move from the colostrum collection device into a barrel of the syringe;
   detaching the colostrum collection device from the syringe; and
   dispensing the colostrum to the newborn from the syringe without transferring the colostrum to any other colostrum container.

2. A method as in claim 1, wherein the coupling step comprises threading the syringe thread on the small-diameter syringe-coupling end of the colostrum collection device into a complementary thread on the syringe.

3. A method as in claim 1, wherein the syringe comprises an enteral syringe, and wherein the coupling step comprises attaching a tapered inner surface on the small-diameter syringe-coupling end of the colostrum collection device with a complementary surface on a distal end of the enteral syringe via press fit.

4. A method as in claim 1, wherein dispensing the colostrum comprises:
   inserting a distal end of the syringe into the newborn's mouth; and
   depressing the plunger of the syringe to force the colostrum out of the distal end and into the newborn's mouth.

5. A method as in claim 1, further comprising:
   attaching the breast shield with the large-diameter colostrum collection end via the breast shield thread;
   applying the breast shield to the breast; and
   expressing milk from the breast and into the colostrum collection device, using the breast pump system.

6. A method of collecting colostrum from a breast of a human and dispensing the colostrum to a newborn, the method comprising:
   providing a colostrum collection device, comprising:
      a colostrum collection member, comprising:
         a proximal funnel-shape portion;
         a distal narrow portion; and
         a cylindrical middle portion between the proximal funnel-shaped portion and the distal narrow portion; and
      a plunger comprising a distal stopper portion;
   manually expressing colostrum from the breast into an open end of the proximal funnel-shaped portion of the colostrum collection member;
   inserting the distal stopper portion of the plunger of the colostrum collection device into the open end of the proximal funnel-shaped portion; and
   depressing the plunger to advance the distal stopper portion through the middle cylindrical portion of the colostrum collection member to force the colostrum through the middle cylindrical portion and out of the distal narrow portion of the colostrum collection member and into the newborn's mouth.

7. A method as in claim 6, further comprising measuring an amount of the expressed colostrum by viewing a fluid level indicator on a side of the colostrum collection member.

* * * * *